(12) United States Patent
Naisby et al.

(10) Patent No.: US 9,823,221 B2
(45) Date of Patent: Nov. 21, 2017

(54) MICROSTRUCTURED POLYMER DEVICES

(71) Applicant: STRATEC Consumables GmbH, Salzburg (AT)

(72) Inventors: Andrew Naisby, Salzburg (AT); Miguel Angel Torello Arevalo, Salzburg (AT); Slavko Glibo, Salzburg (AT)

(73) Assignee: STRATEC Consumables GmbH, Anif (AT)

( * ) Notice: Subject to any disclaimer, the term of this patent is extended or adjusted under 35 U.S.C. 154(b) by 323 days.

(21) Appl. No.: 14/379,209

(22) PCT Filed: Feb. 13, 2013

(86) PCT No.: PCT/EP2013/052893
§ 371 (c)(1),
(2) Date: Aug. 15, 2014

(87) PCT Pub. No.: WO2013/120908
PCT Pub. Date: Aug. 22, 2013

(65) Prior Publication Data
US 2015/0014170 A1    Jan. 15, 2015

(30) Foreign Application Priority Data

Feb. 17, 2012    (EP) .................................... 12156005

(51) Int. Cl.
*G01N 27/447* (2006.01)
*B01L 3/00* (2006.01)
(Continued)

(52) U.S. Cl.
CPC .. *G01N 27/44791* (2013.01); *B01L 3/502707* (2013.01); *C09D 5/24* (2013.01);
(Continued)

(58) Field of Classification Search
CPC ......... B01L 3/502707; B01L 3/502792; C09D 5/24; H05K 3/107; H05K 3/1258; G01N 27/44791
See application file for complete search history.

(56) References Cited

U.S. PATENT DOCUMENTS

| 5,429,735 A | 7/1995 | Johnson et al. |
| 5,439,791 A | 8/1995 | Kok et al. |

(Continued)

FOREIGN PATENT DOCUMENTS

| DE | 197 21 238 | 11/1998 |
| EP | 0 953 420 | 11/1999 |

(Continued)

OTHER PUBLICATIONS

Thomas I. Wallow, et al., "Low-distortion, high-strength bonding of thermoplastic microfluidic devices employing case-II diffusion-mediated permeant activation", Lab Chip, vol. 7, pp. 1825-1831, (2007).

(Continued)

*Primary Examiner* — Daniel McNally
(74) *Attorney, Agent, or Firm* — 24IP Law Group; Timothy R. DeWitt

(57) ABSTRACT

A method of manufacturing a device with a planar electrode structure, the method comprising: (a) forming a microfluidic channel on a substrate; (b) applying a primer layer to at least part of the microfluidic channel, (c) applying a conductive liquid to the microfluidic channel, the conductive liquid comprising electrically conductive particles dispersed in a carrier medium, the carrier medium including a solvent; (d) allowing the conductive liquid to flow throughout the microfluidic channel by capillary action to form the planar electrode structure; and (e) evaporating the solvent from the (Continued)

carrier medium, is described. Devices obtainable using the method and their applications are also described.

15 Claims, 16 Drawing Sheets

(51) Int. Cl.
    *C09D 5/24*     (2006.01)
    *H05K 3/10*     (2006.01)
    *H05K 3/12*     (2006.01)
    *G06K 19/077*     (2006.01)

(52) U.S. Cl.
    CPC ........... *H05K 3/107* (2013.01); *H05K 3/1258* (2013.01); *B01L 3/502792* (2013.01); *B01L 2300/0645* (2013.01); *B01L 2300/0816* (2013.01); *B01L 2400/0415* (2013.01); *B01L 2400/0427* (2013.01); *G06K 19/0775* (2013.01); *H05K 3/1208* (2013.01)

(56) References Cited

U.S. PATENT DOCUMENTS

| | | | |
|---|---|---|---|
| 6,033,202 A | 3/2000 | Bao et al. | |
| 6,322,736 B1 | 11/2001 | Bao et al. | |
| 6,599,408 B1 | 7/2003 | Chan et al. | |
| 6,686,314 B2* | 2/2004 | Xu ............................ | B32B 5/18 156/235 |
| 7,677,701 B2 | 3/2010 | Xiao | |
| 7,709,544 B2 | 5/2010 | Doyle et al. | |
| 7,982,296 B2 | 7/2011 | Nuzzo et al. | |
| 2005/0036020 A1 | 2/2005 | Li et al. | |
| 2006/0065897 A1 | 3/2006 | Hirai et al. | |
| 2006/0074143 A1* | 4/2006 | Rodgers ............... | C09D 11/102 523/160 |
| 2006/0201812 A1 | 9/2006 | Grande et al. | |
| 2009/0078915 A1 | 3/2009 | Lee et al. | |
| 2010/0093105 A1* | 4/2010 | Lee ....................... | B07C 5/3416 436/171 |
| 2010/0137163 A1* | 6/2010 | Link .................. | B01F 13/0071 506/16 |
| 2010/0209318 A1 | 8/2010 | Grande et al. | |
| 2011/0045577 A1* | 2/2011 | Bruzewicz ........ | B01L 3/502707 435/287.1 |
| 2012/0213975 A1 | 8/2012 | Naisby et al. | |

FOREIGN PATENT DOCUMENTS

| | | |
|---|---|---|
| EP | 1 642 945 | 4/2006 |
| EP | 2 028 688 | 2/2009 |
| EP | 2 489 436 | 8/2012 |
| GB | 1 178 745 | 1/1970 |
| JP | 2010 90211 | 4/2010 |
| WO | 00 77509 | 12/2000 |
| WO | 2004 068389 | 8/2004 |
| WO | 2008 069565 | 6/2008 |
| WO | 2011 036509 | 3/2011 |

OTHER PUBLICATIONS

International Search Report dated Jun. 21, 2013 in PCT/EP13/052893 Filed Feb. 13, 2013.
Pangea Search Report.

\* cited by examiner

MICROSTRUCTURED POLYMER DEVICES

CROSS REFERENCE TO RELATED APPLICATION

The present application claims the benefit of the earlier filing dates of EP12156005.6, filed in the European Patent Office on Feb. 17, 2012, and PCT/EP2013/052893, filed on Feb. 13, 2013, the entire content of which applications are incorporated herein by reference.

TECHNICAL FIELD

This technology relates to methods for manufacturing devices having an electrode pattern formed thereon. It also relates to such devices.

BACKGROUND

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present disclosure.

Microfluidic devices, such as micro-structured polymer devices (MPDs), are useful tools for the analysis of chemicals and biological fluids. Microfluidic devices can be formed from plastics compounds, which may be formed by a moulding process. Microfluidic devices typically include fluid transport channels—for example input and output channels—and other fluid flow or storage structures to enable the intended measurement or chemical or biological reaction to take place. For effective analysis of the fluid by the microfluidic device the fluid must controllably pass through these channels.

Microfluidic devices will often include electrodes, i.e. electrically conductive structures, arranged to interact with fluid in the channels or other fluid structures. Examples might be electrodes leading to a measurement sensor, to enable a property of a channel to be measured, and electrodes for receiving an active electrical stimulus, e.g. to receive a voltage signal for manipulating fluid in the MPD by electrowetting or dielectrophoresis.

Various types of microfluidic devices have been proposed. The channel cross-section dimensions in a microfluidic device can vary widely, but may be anything from the millimetre scale to the nanometre scale. Reference to microfluidics in this document is not restricted to micrometre scale devices, but includes both larger (millimetre) and smaller (nanometre) scale devices as well as intermediate (micrometre) scale devices, as is usual in the art.

A basic form of a microfluidic device is based on continuous flow of the relevant fluids through the channels.

A development of this basic form has the active fluid conveyed through the channels in droplets held in suspension by a functionally inert carrier liquid. Some of the devices described herein are droplet-based, microfluidic devices. In such devices, a droplet is formed of a first liquid, the droplet liquid, suspended immiscibly in a second liquid, the carrier liquid. The droplet liquid and the carrier liquid should be selected to be immiscible over the relevant time scale needed for good functioning of the device as determined by factors such as transit time, storage time, and reaction time within the device. Droplets are generally spherical, but in use the droplets may be distorted by forces or constrained by boundaries of the channel or other parts of the microstructured device, so other shapes may exist. A droplet in the context of a digital microfluidic device is therefore a contiguous volume of a fluid held in a carrier liquid, wherein the fluid and the carrier liquid are immiscible.

Microfluidic devices may be made from a variety of substrate materials, including thermoplastic, glass and crystal. In thermoplastic microfluidic devices, the channels can be formed by a variety of means, including injection moulding.

Known ink compositions contain non-volatile solvents, particularly high boiling point polyols such as glycerol. The boiling point of these solvents may range from 80 to 300° C., in some embodiments 100 to 200° C. These components act as humectants to prevent premature drying of the ink in the jetting nozzles to ensure reliability of the jetting process. The sintering is normally a heating step which evaporates the solvent of the conductive liquid. The presence of the high boiling point liquids influences the temperature of the sintering however as any remaining organic component will impede a conductive pathway, thereby producing a product with lower and more variable conductivity. Higher sintering temperatures require a greater energy input and may damage thermoplastic substrates.

It is to be understood that both the foregoing general description of the disclosure and the following detailed description are exemplary, but are not restrictive, of the invention disclosure.

SUMMARY OF THE TECHNOLOGY

The following are provided:

(1) A method of manufacturing a device with an electrode structure, the method comprising:

(a) providing a substrate with a microfluidic channel structure shaped to match the electrode structure;

(b) applying a primer layer to the microfluidic channel structure;

(c) introducing a conductive liquid to the primed microfluidic channel structure, the conductive liquid comprising a carrier medium including a solvent in which electrically conductive particles are dispersed;

(d) waiting for the conductive liquid to flow throughout the microfluidic channel structure by capillary action; and (e) evaporating the solvent from the carrier medium to allow the electrically conductive particles to form the electrode structure.

(2) A method according to (1), further comprising after step (e) the step of:

(f) laminating the substrate with a cap layer to cover at least a part of the electrode structure.

(3) A method according to (2), wherein the carrier medium additionally contains a radiation curable monomer or prepolymer and wherein the method further comprises after step (f) the step of:

(g) applying radiation through the cap layer to cure the radiation curable monomer and thus harden the conductive liquid.

(4) A method according to any of (1) to (3), wherein the radiation curable monomer or prepolymer is curable using visible light.

(5) A method according to any of (1) to (4), wherein the solvent is an organic solvent miscible with water.

(6) A method according to (5), wherein the carrier medium additionally contains water.

(7) A method according to (5) or (6), wherein the organic solvent is an oxygenated solvent selected from an alcohol, a glycol ether and a glycol ester.

(8) A method according to any of (1) to (7), wherein in step (a) a pad is additionally formed on the substrate in fluid communication with the microfluidic channel, and in step (c) the conductive liquid is applied to the pad and distributed to the microfluidic channel structure by capillary action.

(9) A method according to any of (1) to (8), wherein the substrate is an organic polymer.

(10) A method according to any of (1) to (9), wherein in step (a) the substrate with microfluidic channel is formed by injection moulding.

(11) A method according to any of (1) to (10), wherein step (b) of applying the primer layer comprises:

(b1) introducing a primer liquid to the microfluidic channel structure, the primer liquid comprising a primer carrier medium including a primer solvent; and (b2) waiting for the primer liquid to flow throughout the microfluidic channel structure by capillary action.

(12) A method according to any of (1) to (11), wherein the primer layer comprises:

(i) an organic polymer; and
(ii) a porous particulate material, the organic polymer being dispersed in the porous particulate material.

(13) A method according to (12), wherein the organic polymer (i) in the primer layer is selected from the group consisting of:

(a) a polymer including a vinyl lactam repeating unit;
(b) a cellulose ether;
(c) a polyvinyl alcohol; and
(d) unmodified or modified gelatin.

(14) A method according to any of (1) to (11), wherein the primer layer comprises a porous particulate material and does not include an organic polymer.

(15) A device obtainable by the method of any of (1) to (14).

In at least some embodiments, the primer layer absorbs the non-volatile components of the humectant organic solvents in which the electrically conductive material of the conductive liquid is dispersed, so that these components are no longer present in the ink but are absorbed into the primer layer. As demonstrated herein, in at least some embodiments the composition of the primer layer acts as a sieve for the undesired ingredients in the conductive liquid, absorbing these components into the primer layer. This allows the final sintering step to be carried out at a lower temperature than was previously possible in the art. This is particularly applicable when the substrate is formed of a thermoplastic polymer, especially a polyolefin such as cycloolefin polymer.

In at least some embodiments, the primer layer can be applied using a primer liquid and capillary action, similar to how the conductive liquid is applied. Namely, the primer liquid can be introduced to the microfluidic channel structure, for example a droplet can be placed at one or more specific locations in or adjacent to the channel structure, and then allowed to flow by capillary action over the primer layer throughout the microfluidic channel structure. Alternatively, the primer layer can be applied by deposition into the microfluidic channel, e.g. by a printing process such as screen printing or inkjet printing, or evaporation through a mask.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein:

FIG. 16b schematically illustrates the dispensed area (pad area only) of the electrode pattern of FIG. 16a;

DETAILED DESCRIPTION

Definitions

Figure 1A:
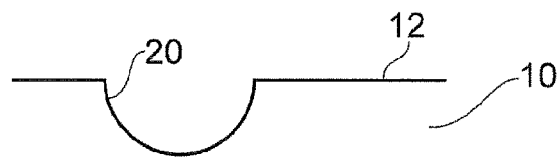
FIGS. 1A to 1G are schematic sections through a substrate showing in sequence steps in the manufacture of an electrode in a channel according to an embodiment of the technology.

In this specification "alkyl" denotes a straight- or branched-chain, saturated, aliphatic hydrocarbon radical. Said "alkyl" may consist of 1 to 12, typically 1 to 8, in some embodiments 1 to 6 carbon atoms. A $C_{1-6}$ alkyl group includes methyl, ethyl, propyl, isopropyl, butyl, t-butyl, 2-butyl, pentyl, hexyl, and the like. The alkyl group may be substituted where indicated herein.

"Cycloalkyl" denotes a cyclic, saturated, aliphatic hydrocarbon radical. Examples of cycloalkyl groups are moieties having 3 to 10, for example 3 to 8 carbon atoms including cyclopropyl, cyclobutyl, cyclopentyl, cyclohexyl and cyclooctyl groups. The cycloalkyl group may be substituted where indicated herein.

"Alkoxy" means the radical "alkyl-O-", wherein "alkyl" is as defined above, either in its broadest aspect or a more restricted aspect.

"Phenyl" means the radical —C$_6$H$_5$. The phenyl group may be substituted where indicated herein.

"Hydroxy" means the radical —OH.

"Thiol" means the radical —SH.

"Halo" means a radical selected from fluoro, chloro, bromo, or iodo.

"Nitro" means the radical —NO$_2$.

"Carboxylic acid" means the radical —CO$_2$H.

"Sulfinic acid" means the radical —SO$_2$H.

"Sulfonic acid" means the radical —SO$_3$H.

"Amino" means the radical —NR$_2$, wherein R is hydrogen or alkyl (as defined above, either in its broadest aspect or a more restricted aspect).

Substrate

The device of the present technology has a planar electrode structure and is formed on a substrate. The substrate is not particularly critical to the present technology provided it is compatible with the primer layer and the conductive liquid. Examples of suitable substrates include glasses, particularly epoxy glasses, and thermoplastic organic polymers.

In one embodiment, the substrate is a thermoplastic organic polymer. Suitable thermoplastic organic polymers that can be used to provide the substrate include, but are not limited to, polymers formed from monomers having ethylenically unsaturated groups (in particular polyolefins), polyamides (nylons), polyesters, polycarbonates, polyimides and mixtures thereof.

Examples of suitable polymers formed from ethylenically unsaturated monomers include polyolefins, which include, but are not limited to: polyethylenes; polypropylenes; poly (1-butene); poly(methyl pentene); poly(vinyl chloride); poly (acrylonitrile); poly(tetrafluoroethylene) (PTFE-Teflon®), poly(vinyl acetate); polystyrene; poly(methyl methacrylate); ethylene-vinyl acetate copolymer; ethylene methyl acrylate copolymer; styrene-acrylonitrile copolymers; cycloolefin polymers and copolymers; and mixtures and derivatives thereof. Examples of suitable polyethylenes include, but are not limited to, low density polyethylene, linear low density polyethylene, high density polyethylene, ultra-high molecular weight polyethylene, and derivatives thereof.

Examples of suitable polyamides include nylon 6-6, nylon 6-12 and nylon 6. Examples of suitable polyesters include polyethylene terephthalate, polybutylene terephthalate, polytrimethylene terephthalate, polyethylene adipate, polycaprolactone, and polylactic acid.

In some embodiments, the thermoplastic organic polymer is a polyolefin, in particular. a cycloolefin homopolymer or copolymer. In this specification the term "cycloolefin homopolymer" means a polymer formed entirely from cycloalkene (cycloolefin) monomers. Typically, the cycloalkene monomers from which the cycloolefin homopolymer is formed have 3 to 14, in some embodiments 4 to 12, in some embodiments 5 to 8, ring carbon atoms. Typically, the cycloalkene monomers from which the cycloolefin homopolymer is formed have 1 to 5, such as 1 to 3, in some embodiments 1 or 2, in some embodiments 1 carbon-carbon double bonds. Typically, the cycloalkene monomers from which the cycloolefin homopolymer is formed have 1 to 5, such as 1 to 3, in some embodiments 1 or 2, in some embodiments 1 carbocyclic ring. The carbocyclic ring may be substituted with one or more, typically 1 to 3, in some embodiments 1 or 2, in some embodiments 1 substituent, the substituent(s) being each independently selected from the group consisting of C$_{1-6}$ alkyl (typically C$_{1-4}$ alkyl, particularly methyl or ethyl), C$_{3-8}$ cycloalkyl (typically C$_{5-7}$ cycloalkyl, especially cyclopentyl or cyclohexyl), phenyl (optionally substituted by 1 to 5 substituents selected from C$_{1-6}$ alkyl, C$_{1-6}$ alkoxy, halo and nitro), or halogen.

The term "cycloolefin copolymer" means a polymer formed from both cycloalkene and non-cyclic alkene (olefin) monomers. The monomers may be hydrocarbons or may have additional functional groups, provided they contain an ethylenically unsaturated (C=C) bond. Typically, the cycloalkene monomers from which the cycloolefin copolymer is formed have 3 to 14, in some embodiments 4 to 12, in some embodiments 5 to 8, ring carbon atoms. Typically, the cycloalkene monomers from which the cycloolefin coopolymer is formed have 1 to 5, such as 1 to 3, in some embodiments 1 or 2, in some embodiments 1 carbon-carbon double bonds. Typically, the cycloalkene monomers from which the cycloolefin copolymer is formed have 1 to 3, in some embodiments 1 or 2, in some embodiments 1 carbocyclic ring. The carbocyclic ring may be substituted with one or more, typically 1 to 3, in some embodiments 1 or 2, in some embodiments 1 substituent, the substituent(s) being each independently selected from the group consisting of C$_{1-6}$ alkyl (typically C$_{1-4}$ alkyl, particularly methyl or ethyl), C$_{3-8}$ cycloalkyl, (typically C$_{5-7}$ cycloalkyl, especially cyclopentyl or cyclohexyl), phenyl (optionally substituted by 1 to 5 substituents selected from C$_{1-6}$ alkyl, C$_{1-6}$ alkoxy, halo and nitro), or halogen. Examples of the non-cyclic alkene copolymerised with the cycloolefin include ethylene; propylene; 1-butene; 2-methylpentene; vinyl chloride; acrylonitrile; tetrafluoroethylene; vinyl acetate; styrene; methyl methacrylate and methyl acrylate, in some embodiments ethylene or propylene, particularly ethylene.

Examples of commercially available cycloolefin homopolymers and copolymers usable in the present technology are those based on 8,8,10-trinorborn-2-ene (norbornene; bicyclo [2.2.1]hept-2-ene) or 1,2,3,4,4a,5,8,8a-octahydro-1,4:5,8-dimethanonapthalene (tetracyclododecene) as monomers. As described in Shin et al., *Pure Appl. Chem.*, 2005, 77(5), 801-814, homopolymers of these monomers can be formed by a ring opening metathesis polymerisation: copolymers are formed by chain copolymerisation of the aforementioned monomers with ethylene.

Therefore, in one embodiment, the cycloolefin polymer is a cycloolefin homopolymer of general formula (A):

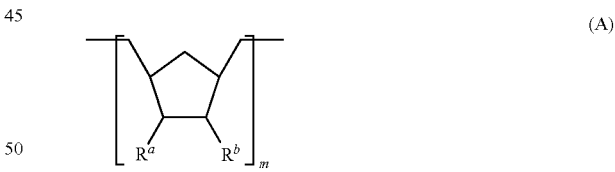

(A)

wherein:

m is such that the average molecular weight (M$_w$) of the polymer ranges from 25,000 to 250,000; and R$^a$ and R$^b$ are each independently selected from the group consisting of:

hydrogen;

C$_{1-6}$ alkyl (the alkyl group being optionally substituted by 1 to 3 substituents independently selected from C$_{3-8}$ cycloalkyl, C$_{1-6}$ alkoxy, hydroxy, halo, —NH$_2$, —NH(C$_{1-6}$ alkyl), —N(C$_{1-6}$ alkyl)$_2$, —C(=O)OH or —C(=O)C$_{1-6}$ alkyl);

C$_{3-8}$ cycloalkyl (the cycloalkyl group being optionally substituted by 1 to 3 substituents independently selected from C$_{1-6}$ alkyl, C$_{1-6}$ alkoxy, hydroxy, halo, —NH$_2$, —NH (C$_{1-6}$ alkyl), —N(C$_{1-6}$ alkyl)$_2$, —C(=O)OH or —C(=O) C$_{1-6}$ alkyl);

phenyl (optionally substituted by 1 to 5 substituents selected from $C_{3-8}$ cycloalkyl, $C_{1-6}$ alkoxy, hydroxy, halo, —$NH_2$, —$NH(C_{1-6}$ alkyl), —$N(C_{1-6}$ alkyl$)_2$, —$C(=O)OH$, —$C(=O)C_{1-6}$ alkyl and nitro), $C_{1-6}$ alkoxy;

hydroxy;

halo;

—$NH_2$,

—$NH(C_{1-6}$ alkyl),

—$N(C_{1-6}$ alkyl$)_2$,

—$C(=O)OH$; or

—$C(=O)C_{1-6}$ alkyl;

or $R^a$ and $R^b$ together with the carbon atoms to which they are attached form a carbocyclic ring having 4 to 10, in some embodiments 5 to 8, carbon atoms in 1 to 3, in some embodiments 1 or 2, rings, the ring carbon atoms each being optionally substituted by one or more substituents selected from the group consisting of:

$C_{1-6}$ alkyl (the alkyl group being optionally substituted by 1 to 3 substituents independently selected from $C_{3-8}$ cycloalkyl, $C_{1-6}$ alkoxy, hydroxy, halo, —$NH_2$, —$NH(C_{1-6}$ alkyl), —$N(C_{1-6}$ alkyl$)_2$, —$C(=O)OH$ or —$C(=O)C_{1-6}$ alkyl), $C_{3-8}$ cycloalkyl (the cycloalkyl group being optionally substituted by 1 to 3 substituents independently selected from $C_{1-6}$ alkyl, $C_{1-6}$ alkoxy, hydroxy, halo, —$NH_2$, —$NH(C_{1-6}$ alkyl), —$N(C_{1-6}$ alkyl$)_2$, —$C(=O)OH$ or —$C(=O)C_{1-6}$ alkyl), phenyl (optionally substituted by 1 to 5 substituents selected from $C_{3-8}$ cycloalkyl, $C_{1-6}$ alkoxy, hydroxy, halo, —$NH_2$, —$NH(C_{1-6}$ alkyl), —$N(C_{1-6}$ alkyl$)_2$, —$C(=O)OH$, —$C(=O)C_{1-6}$ alkyl and nitro), $C_{1-6}$ alkoxy, hydroxy, halo,

—$NH_2$, $NH(C_{1-6}$ alkyl),

—$N(C_{1-6}$ alkyl$)_2$,

—$C(=O)OH$ or

—$C(=O)C_{1-6}$ alkyl.

In one embodiment, $R^a$ and $R^b$ are each independently selected from the group consisting of hydrogen, $C_{1-6}$ alkyl, $C_{3-8}$ cycloalkyl or phenyl. In one embodiment, $R^a$ and $R^b$ are each independently selected from the group consisting of hydrogen or $C_{1-6}$ alkyl. In one embodiment, $R^a$ and $R^b$ are both hydrogen.

In an alternative embodiment, $R^a$ and $R^b$ together with the carbon atoms to which they are attached form a ring selected from cyclopentane, cyclohexane, cycloheptane, cyclooctane, bicyclo[2.2.1]heptane or bicyclo[2.2.2]octane, the ring carbon atoms each being optionally substituted by one or more substituents selected from the group consisting of $C_{1-6}$ alkyl (the alkyl group being optionally substituted by 1 to 3 substituents independently selected from $C_{3-8}$ cycloalkyl, $C_{1-6}$ alkoxy, hydroxy, halo, —$NH_2$, —$NH(C_{1-6}$ alkyl), —$N(C_{1-6}$ alkyl$)_2$, —$C(=O)OH$ or —$C(=O)C_{1-6}$ alkyl), $C_{3-8}$ cycloalkyl (the cycloalkyl group being optionally substituted by 1 to 3 substituents independently selected from $C_{1-6}$ alkyl, $C_{1-6}$ alkoxy, hydroxy, halo, —$NH_2$, —$NH(C_{1-6}$ alkyl), —$N(C_{1-6}$ alkyl$)_2$, —$C(=O)OH$ or —$C(=O)C_{1-6}$ alkyl), phenyl (optionally substituted by 1 to 5 substituents selected from $C_{3-8}$ cycloalkyl, $C_{1-6}$ alkoxy, hydroxy, halo, —$NH_2$, —$NH(C_{1-6}$ alkyl), —$N(C_{1-6}$ alkyl$)_2$, —$C(=O)OH$, —$C(=O)C_{1-6}$ alkyl and nitro), $C_{1-6}$ alkoxy, hydroxy, halo, —$NH_2$, —$NH(C_{1-6}$ alkyl), —$N(C_{1-6}$ alkyl$)_2$, —$C(=O)OH$ or —$C(=O)C_{1-6}$ alkyl. In this embodiment, $R^a$ and $R^b$ together with the carbon atoms to which they are attached form a ring selected from cyclopentane, cyclohexane, cycloheptane, cyclooctane, bicyclo[2.2.1]heptane or bicyclo[2.2.2]octane, the ring carbon atoms each being optionally substituted by one or more substituents selected from the group consisting of $C_{1-6}$ alkyl, $C_{3-8}$ cycloalkyl or phenyl.

In some embodiments, m is such that the average molecular weight (Mw) of the polymer ranges from 50,000 to 150,000.

In another embodiment, the cycloolefin polymer is a cycloolefin polymer of formula (B):

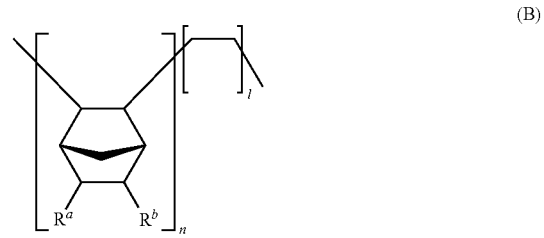

(B)

wherein:

n and l are such that the average molecular weight ($M_w$) of the polymer ranges from 25,000 to 250,000;

n is such that the mole fraction of cycloolefin repeating units ranges from 0.2 to 0.7;

l is such that the mole fraction of ethylene repeating units ranges from 0.8 to 0.3; and $R^a$ and $R^b$ are as defined above for formula (A), either in its broadest aspect or a more restricted aspect.

Chemical structures of the repeating units of certain specific cycloolefin homopolymers useful in the present technology are shown below.

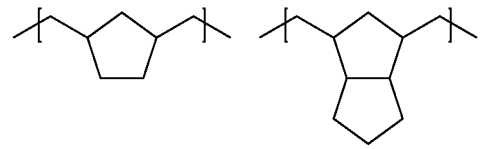

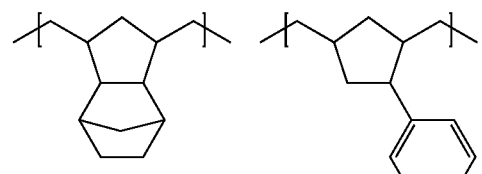

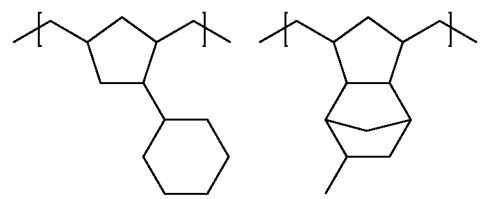

An example of a ring opening metathesis polymerisation scheme for norbornene derivatives, as well as a scheme for their copolymerisation with ethene is shown below.

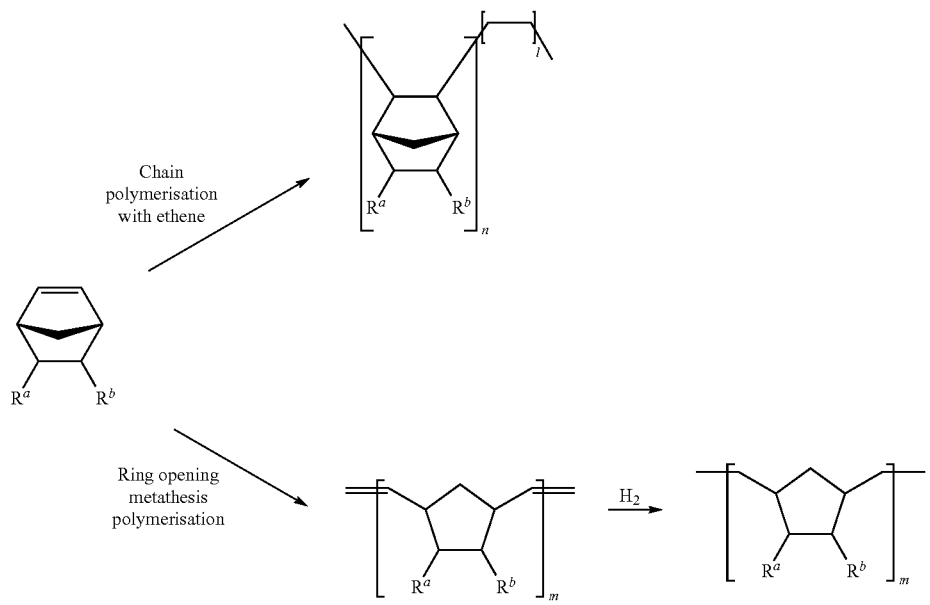

In the above reaction scheme, l, m, n, $R^a$ and $R^b$ are as defined above, either in its broadest aspect or a more restricted aspect.

In some embodiments, n and l are such that the average molecular weight ($M_w$) of the polymer ranges from 50,000 to 150,000.

In some embodiments, n is such that the mole fraction of cycloolefin repeating units ranges from 0.3 to 0.6; and l is such that the mole fraction of ethylene repeating units ranges from 0.7 to 0.4.

Another class of materials known to be suitable for microfluidic device substrates is the class of silicone polymers polydimethylsiloxane (PDMS). These polymers have the general formula:

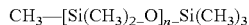

$CH_3$—$[Si(CH_3)_2$—$O]_n$—$Si(CH_3)_3$ where n is the number of repeating monomer $[SiO(CH_3)_2]$ units.

In the above formula, n is such that the average molecular weight (Mw) of the polymer ranges from 100 to 100,000, in some embodiments 100 to 50,000.

Examples of suitable glasses that can be used to provide the substrate include silica glasses, in particular phosphosilicate glass compounds and borosilicate glass compounds.

In another embodiment, the substrate may be a glass-reinforced epoxy laminate. This is a composite material composed of woven fibreglass cloth with an epoxy resin binder. Such composite materials are generally known in the art under the grade designation FR-4.

In this embodiment, the fibreglass (also called glass-reinforced plastic, glass-fibre reinforced plastic, or GFRP) is a fibre reinforced polymer made of a plastic matrix reinforced by fine fibres of glass. The polymer may be epoxy (as defined and exemplified below), a thermosetting plastic (in some embodiments polyester, as defined and exemplified above, or vinylester, which is a resin produced by the esterification of an epoxy resin with an unsaturated monocarboxylic acid) or thermoplastic (as defined and exemplified above).

As is known to those skilled in the art, the epoxy resin used in this technology may be formed by copolymerising a resin with an activator. The resin consists of monomers or prepolymers having more than one epoxide group, the epoxide groups generally being present at terminal ends of the molecule. The activator is then applied to cleave the epoxy groups of the prepolymer and cross-link the polymer.

A typical prepolymer resin is a compound of the formula:

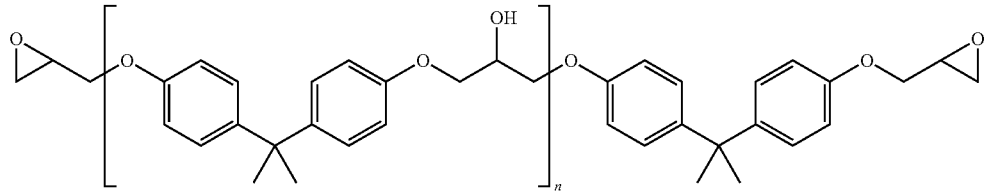

where n denotes the number of polymerized subunits and is in the range from 0 to about 25.

Typically, the resin is formed by reacting an epoxy monomer with a polyol. The "epoxy monomer" is a compound having an epoxy group and a leaving group displaceable by a hydroxyl group (which may be, for example a halogen atom, such as chlorine, bromine or iodine, or a sulfonyloxy group, such as methanesulfonyloxy, benzenesulfonyloxy or p-toluenesulfonyloxy). A particular example of an epoxy monomer is epichlorohydrin. A polyol is an organic compound having more than one hydroxy group. In some embodiments, the polyol is a polyphenol, i.e. a compound having two or more benzene rings, each substituted with at least one hydroxy group. A particular example of a polyol is 4,4'-(propane-2,2-diyl)diphenol (bisphenol-A). When the polyol reacts with the epoxy monomer, the leaving groups of the epoxy monomer are displaced by the polyol hydroxy groups to provide the monomer or prepolymer of the resin referred to above.

Other epoxy resins include multifunctional epoxy resins, alicyclic epoxy resins, brominated epoxy resins, and epoxy-novolac resins. Generally, the epoxy resin is not particularly limited provided it contains more than one epoxy group in the prepolymer molecule.

The activator may be any activator conventionally used to cure epoxy resin prepolymers. Examples of the activator which reacts with the epoxy groups of the uncured epoxy resin prepolymer to cure the resin include amines, imidazoles, amides, esters, alcohols, thiols, ethers, thioethers, phenols, phosphorus compounds, ureas, thioureas, acid anhydrides, Lewis acids, onium salts, active silica compounds-aluminium complex.

Examples of suitable classes of amines include aliphatic amines, alicyclic and heterocyclic amines, aromatic amines, modified amines and the like.

Examples of aliphatic amines include ethylenediamine, trimethylenediamine, tetramethylenediamine, hexamethylenediamine, diethylenetriamine, triethylenetetramine, tetraethylenepentamine, dipropylenediamine, dimethylaminopropylamine, diethylaminopropylamine, trimethylhexamethylenediamine, pentanediamine, bis(2-dimethylaminoethyl)ether, pentamethyldiethylenetriamine, alkyl-t-monoamine, 1,4-diazabicyclo(2.2.2)octane (triethylenediamine), N,N,N',N'-tetramethylhexamethylenediamine, N,N,N',N'-tetramethylpropylenediamine, N,N,N',N'-tetramethylethylenediamine, N,N-dimethylcyclohexylamine, dimethylamino-ethoxyethoxyethanol, and dimethylaminohexanol.

Examples of alicyclic and heterocyclic amines include piperidine, menthanediamine, isophoronediamine, methylmorpholine, ethylmorpholine, N,N',N''-tris(dimethylaminopropyl)hexahydro-s-triazine, N-aminoethylpiperidine, trimethylaminoethyl-piperidine, bis(4-aminocyclohexyl)methane, N,N'-dimethylpiperidine and 1,8-diazabicyclo(4.5.0)undec-7-ene.

Examples of aromatic amines include o-phenylenediamine, m-phenylenediamine, p-phenylenediamine, diaminodiphenylmethane, diaminodiphenylsulfone, benzylmethylamine, dimethylbenzylamine, m-xylenediamine, pyridine and picoline.

Examples of modified polyamines include polyamines added with epoxy compounds, polyamines added by Michael reaction, polyamines added by Mannich reaction, polyamines added with thiourea and ketone-blocked polyamines. Examples of other suitable amines include dicyandiamide, guanidine, organic acid hydrazides, diaminomaleonitrile, amineimide, trifluoroboron-piperidine complex and trifluoroboron-monoethylamine complex.

Examples of imidazole compounds include imidazole, 2-methylimidazole, 2-ethylimidazole, 2-isopropylimidazole, 2-n-propylimidazole, 2-undecyl-1H-imidazole, 2-heptadecyl-1H-imidazole, 1,2-dimethylimidazole, 2-ethyl-4-methylimidazole, 2-phenyl-1H-imidazole, 4-methyl-2-phenyl-1H-imidazole, 2-phenyl-4-methylimidazole, 1-benzyl-2-methylimidazole, 1-cyanoethyl-2-methylimidazole, 1-cyanoethyl-2-ethyl-4-methylimidazole, 1-cyanoethyl-2-undecylimidazole, 1-cyanoethyl-2-phenylimidazole, 1-cyanoethyl-2-ethyl-4-methylimidazolium trimellitate, 1-cyanoethyl-2-undecylimidazolium trimellitate, 1-cyanoethyl-2-phenylimidazolium trimellitate, 2,4-diamino-6-[2'-methylimidazolyl-(1')]-ethyl-s-triazine, 2,4-diamino-6-(2'-undecyl-imidazolyl)-ethyl-s-triazine, 2,4-diamino-6-[2'-ethyl-4-imidazolyl-(1')]-ethyl-s-triazine, 2,4-diamino-6-[2'-methylimidazolyl-(1')]-ethyl-s-triazine isocyanuric acid addition products, 2-phenylimidazole isocyanuric acid addition products, 2-methylimidazole isocyanuric acid addition products, 2-phenyl-4,5-dihydroxymethylimidazole, 2-phenyl-4-methyl-5-hydroxymethylimidazole, 1-cyanoethyl-2-phenyl-4,5-di(2-cyanoethoxy)-methylimidazole, 1-dodecyl-2-methyl-3-benzylimidazolium chloride, 1-benzyl-2-phenylimidazole hydrochloride and 1-benzyl-2-phenylimidazolium trimellitate.

Examples of imidazoline compounds include 2-methylimidazoline and 2-phenylimidazoline.

Examples of amide compounds include polyamides obtainable by means of polymerization of a dicarboxylic acid and a polyamine. Examples of ester compounds include active carbonyl compounds, such as aryl and thioaryl esters of carboxylic acids. Examples of phenols, alcohols, thiols, ethers and thioether compounds include phenol novolac, cresol novolac, polyols, polymercaptans, polysulfides, 2-(dimethylaminomethylphenol), 2,4,6-tris(dimethylaminomethyl)phenol, and tri-2-ethylhexyl hydrochloride of 2,4,6-tris(dimethylaminomethyl)phenol.

In one embodiment, the activator is a polyamine monomer. The amine groups on the activator may be primary, secondary, tertiary, or a mixture thereof. Examples of suitable polyamines include ethylenediamine, diethylenetriamine, triethylene-tetramine, and diaminodiphenylmethane. When the resin and activator are mixed together, the amine groups react with the epoxide groups to form a covalent bond. Each NH group can react with an epoxide group, so that the resulting polymer is heavily cross-linked.

Crystal substrates, in particular semiconductor substrates, such as silicon substrates, may also be used. Another suitable crystal for the substrate is lithium niobate.

Primer Layer

The devices of the present technology also include a primer layer. In the methods of the present technology, following formation of the microfluidic channel in step (a), in step (b) the primer layer is then applied to at least part of the microfluidic channel. The primer layer is capable of absorbing the humectant organic solvent (particularly although not exclusively the higher boiling point components thereof) in which the metal particles of the conductive liquid are dispersed. This allows the subsequent sintering to be carried out at a much lower temperature than was previously possible in the art: this is particularly advantageous for thermoplastic substrates as it avoids overheating and possible damage to the substrate. The primer layer should also have a low viscosity (typically 5 to 500 mPa·s; in some embodiments 5 to 100 mPa·s) and should be soluble in and/or at least compatible with in the dispensing solvent used to obtain optimal fluidic flow into the channels.

The primer layer comprises a porous particulate material with or without an organic polymer, as defined and exemplified below. The primer layer is capable of interacting with all of the conductive liquids described below.

In one embodiment, the primer layer comprises a porous particulate material dispersed in an organic polymer. The organic polymer acts as a binder for the porous particulate material and has a high cohesive strength. The organic polymer contains hydrophilic functional groups (such as hydroxyl, amino, carbonyl, carboxyl, carboxylic ester, sulfone, sulfonic acid) capable of bonding to the hydrophilic functional groups (especially the hydroxyl groups) in the organic solvent. Such groups therefore enable the polymer to bind the molecules of the humectant organic solvent. In some embodiments, the polymer also has at least partial solubility in the humectant organic solvent of the conductive liquid: this further serves to absorb the less volatile components present in the fluid, hence leaving a purer electrically conductive layer on the surface of the primer after printing.

In some embodiments, the primer layer contains up to 30%, in some embodiments up to 25%, in some embodiments up to 20%, in some embodiments up to 15%, and in some embodiments up to 10% of the organic polymer, the percentage being expressed as a percentage by weight of the concentrated primer, before dissolution in solvent(s).

In some embodiments, the primer layer contains 1 to 30%, in some embodiments 2 to 25%, and in some embodiments 5 to 15% of the organic polymer the percentage being expressed as a percentage by weight of the concentrated primer before dissolution in solvent(s).

In one embodiment, the organic polymer is a polymer including a vinyl lactam repeating unit (also referred to herein as a "vinyl lactam polymer"), i.e. a polymer including a repeating unit of the following general formula (I):

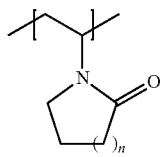

(I)

wherein n is 0 to 6.

In some embodiments n is 1, 2 or 3, in some embodiments 1 or 3, in some embodiments 1. When n is 1, the repeating unit is a vinyl pyrrolidone repeating unit. When n is 3, the repeating unit is a vinyl caprolactam repeating unit.

The vinyl lactam polymer may be a homopolymer (i.e. where the vinyl lactam is the only repeating unit) or a copolymer including another vinyl repeating unit in addition to the vinyl lactam repeating unit. When the vinyl lactam polymer is a copolymer, the other repeating unit may be any known vinyl repeating unit; examples include: ethylene; propylene; 1-butene; 2-methylpentene; acrylonitrile; vinyl acetate; styrene; methyl methacrylate; methyl acrylate; an alkylaminomethacrylate; an alkylaminomethacrylamide; and mixtures thereof. The vinyl repeating units all have carbon-carbon double bonds in their monomeric form; these are broken to bond together the repeating units of the polymer in which the carbon atoms are singly bonded.

When the organic polymer is a copolymer containing a vinyl lactam repeating unit, the copolymer typically contains at least 30%, in some embodiments at least 40%, vinyl lactam repeating units (as a percentage of the total number of repeating units in the copolymer).

Examples of copolymer types include: alternating copolymers (where the repeating A and B units alternate A-B-A-B-A-B); block copolymers which comprise two or more homopolymer subunits linked by covalent bonds (AAAAAAAA-BBBBBBBB-AAAAAAA-BBBBBBB) and random copolymers where the repeating A and B units are distributed randomly. In some embodiments, the copolymers used in the present technology are random copolymers.

In some embodiments, the organic polymer is a homopolymer or copolymer of vinyl pyrrolidone. In one embodiment, the organic polymer is polyvinyl pyrrolidone (ie a homopolymer wherein vinyl pyrrolidone is the only repeating unit). In another embodiment, the organic polymer is a copolymer including another vinyl repeating unit; examples include ethylene; propylene; 1-butene; 2-methylpentene; acrylonitrile; vinyl acetate; styrene; methyl methacrylate; methyl acrylate; an alkylaminomethacrylate; an alkylaminomethacrylamide; and mixtures thereof.

When the organic polymer is a copolymer containing a vinyl pyrrolidone repeating unit, the copolymer typically contains at least 30%, in some embodiments at least 40%, vinyl pyrrolidone repeating units (as a percentage of the total number of repeating units in the copolymer).

In one embodiment, the organic polymer is a copolymer including an acrylic or methacrylic repeating unit in addition to the vinyl lactam (in some embodiments vinyl pyrrolidone) repeating unit. In this specification the terms "acrylic repeating unit" or "methacrylic repeating unit" mean the repeating unit of general formula (II):

(II)

wherein R is H or methyl, and

Y is: $OR^1$ or $NR^1R^1$ wherein each $R^1$ is H or $C_{1-6}$ alkyl (optionally substituted with one or more groups selected from halogen, OR' or NR'R' wherein each R' is independently hydrogen or $C_{1-6}$ alkyl).

When R is H, the repeating unit is an acrylic repeating unit. When R is methyl, the repeating unit is a methacrylic repeating unit.

In some embodiments, the acrylic or methacrylic repeating unit is an alkylaminomethacrylate or alkylaminomethacrylamide repeating unit. Such repeating units have the general formula (III):

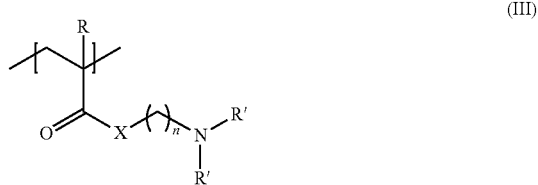

(III)

wherein:
R is hydrogen or methyl;
X is O or NR", wherein R" is hydrogen or $C_{1-6}$ alkyl;
n is 1 to 10; and
each R' is independently H or $C_{1-6}$ alkyl.

When X is O, the repeating unit is an alkylaminomethacrylate repeating unit. When X is NR", the repeating unit is an alkylaminomethacrylamide repeating unit.

In this embodiment, R may be methyl.

In this embodiment, n may be 1 to 4, particularly 2 or 3.

In some embodiments, one or both groups R' are H or methyl, particularly methyl.

In a particular embodiment, the organic polymer is a copolymer of vinyl pyrrolidone and dimethylaminoethylmethacrylate. Such a copolymer is commercially available as Copolymer 958™ from ISP Corporation, New Jersey, USA. Typically, Copolymer 958 comprises 40-60% vinyl pyrrolidone repeating units and 60%-40% dimethylaminoethylmethacrylate repeating units.

In an alternative embodiment, the organic polymer may comprise a blend of polymers:

(1) a polymer containing a vinyl lactam repeating unit, as defined and exemplified above, either in its broadest aspect or a more restricted aspect; and (2) an acrylic polymer. In this context the term "acrylic polymer" means a polymer comprising acrylic or methacrylic repeating units (as defined and exemplified above, either in its broadest aspect or a more restricted aspect). The acrylic polymer may be a homopolymer (i.e. a polymer consisting only of one type of acrylic or methacrylic repeating unit) or a copolymer (i.e. a polymer comprising one or more other repeating units in addition to the acrylic or methacrylic repeating unit; the additional repeating unit may be any of the vinyl repeating units defined and exemplified above). In some embodiments, the acrylic polymer is an acrylic homopolymer, especially methyl methacrylate.

In one embodiment, the organic polymer is a cellulose ether. In this specification "cellulose" means the polysaccharide consisting of a linear chain of about 100 to about 100,000 (in some embodiments 500 to 50,000) β(1→4) linked D-glucose units. Cellulose ethers are cellulose derivatives wherein one or more of the hydroxyl groups of the cellulose molecule are alkylated with an alkyl group (as defined and exemplified above; in some embodiments $C_{1-6}$ alkyl; in some embodiments $C_{1-4}$ alkyl), the alkyl group being optionally substituted with a group selected from $C_{1-6}$ alkoxy, hydroxyl and —$CO_2H$ or —$CO_2(C_{1-6}$alkyl). The alkyl groups may be the same or different; a cellulose ether may have one or more different alkyl groups on the same molecule. Typical examples include methylcellulose, ethylcellulose, ethyl methyl cellulose, hydroxyethyl cellulose, hydroxypropyl cellulose, hydroxyethyl methyl cellulose, hydroxypropyl methyl cellulose (HPMC), ethyl hydroxyethyl cellulose and carboxymethyl cellulose. Hydroxypropyl cellulose and hydroxypropyl methyl cellulose are examples in some embodiments.

In one embodiment, the organic polymer is a polyvinyl alcohol. As is known in the art, polyvinyl alcohol is prepared by first preparing a polyvinyl ester such as polyvinyl acetate followed by partial or complete hydrolysis of the ester bonds in the polyvinyl ester to leave the polymer substituted with hydroxyl groups. The degree of hydrolysis may vary from 30 molar % to 100 molar % (i.e. complete hydrolysis so only hydroxyl groups are present on the polymer). The molar % degree of hydrolysis of the polyvinyl alcohol may be measured using one of the following test methods: International Standards ISO 15023-1:2001, ISO 15023-2:2003 and Japanese Industrial Standard (JIS) K6726.

In some embodiments, the polyvinyl alcohol used in the present technology has a degree of hydrolysis of between 30 and 99 molar %: in some embodiments 35 to 95 molar %.

In one embodiment, the polyvinyl alcohol used in the present technology has a degree of hydrolysis of 40 to 80 molar %, in some embodiments 50 to 70 molar %. Polyvinyl alcohols having this degree of hydrolysis have been found to absorb the humectant organic solvent in the conductive liquid most effectively and be most soluble in the organic solvents used for micro-dispensing a primer layer.

In one embodiment, the polyvinyl alcohol used in the present technology has a degree of hydrolysis of 75 to 95 molar %, in some embodiments 80 to 90 molar %. Polyvinyl alcohols having this degree of hydrolysis have been found to confer optimum printability on the conductive liquid but have limited solubility in the organic solvents used for micro dispensing a primer layer. Therefore the degree of hydrolysis for polyvinyl alcohol in the present technology may be, for example, 70-90 molar %.

As is known in the art, the degree of hydrolysis determines the degree of crystallinity of a polyvinyl alcohol polymer. The degree of crystallinity may also depend on a number of factors such as stereoregularity (tacticity), degree of branching and the crystalline melting point/glass transition temperature. Without wishing to be bound by theory, it is also proposed that the degree of crystallinity of polyvinyl alcohol can vary whilst maintaining a constant degree of hydrolysis, thereby improving the polymer's solubility in the organic solvents contained in the present technology. An example polymer exhibiting a good compromise for solubility in organic solvents used for micro-dispensing and optimum printability of a conductive liquid is commercially available from Nippon Gohsei under the trade name Nichigo G-Polymer, specifically Nichigo G-Polymer OKS 8041.

In one embodiment, the organic polymer used in the primer layer is unmodified or modified gelatin. As is known to those skilled in the art, gelatin comprises a mixture of polypeptides and proteins. As indicated in "The Science and Technology of gelatin", (Food Science & Technology Monographs) ed. A. G. Ward A. Courts, 13 Jun. 1977 (the contents of which are incorporated herein by reference), the molecular weight of the proteins and polypeptides can vary from 30,000 to 300,000 g/mol.

Gelatin is typically produced by degradation of collagen. Collagen is a protein which may be extracted from sources such as bones, skin, connective tissues, organs and some intestines of animals such as domesticated cattle, chicken, and pigs. The degradation of collagen to produce gelatin may be carried out using a number of possible reagents known to those skilled in the art, including but not limited to acids, bases and enzymes.

As is known to those skilled in the art, gelatin is capable of modification by reaction of the free hydroxyl groups and amino groups with a suitable reagent. For example, the hydroxyl groups may be etherified by substitution of the hydrogen with an alkyl group, or esterified by substitution of the hydrogen with an acyl group, or acetalised by condensation of two hydroxyl groups with a carbonyl-containing compound. Examples of suitable reagents include alkylating agents, such as alkyl halides or sulfonates, acylating agents, such as acid chlorides and acid anhydrides, and carbonyl compounds, such as, aldehydes and ketones. The reaction of gelatin with aldehydes may lead to crosslinking to cure the polymer. Reaction with acylating agents, such as acid anhydrides, may lead to a change in the properties of the gelatin, including its chemical or thermal stability.

In some embodiments, the modified gelatin is an acyl-modified gelatin, especially a succinyl-modified gelatin and particularly an alkylsuccinyl-modified gelatin. Examples of suitable modified gelatins are described in DE 19721238A and US 5439791, the contents of which are incorporated herein by reference. A particular example is the photographic gelatin available from GELITA®.

In some embodiments, the organic polymer used in the primer layer is cross-linked. Cross-linking the primer after formation of the electrode pattern increases the dimensional and environmental stability of the final electrode pattern on the microfluidic device. Examples of suitable curing agents are polyaminoamide-epichlorohydrin resins, also melamine and benzoguanamine derivatives—according to the general chemical formulae:

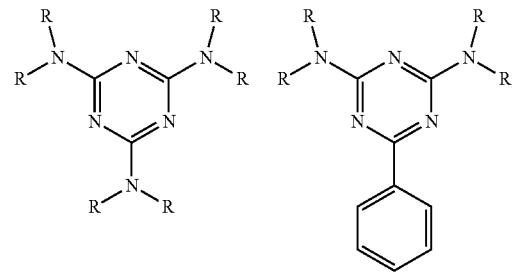

where R = H, —$OCH_3$, —$OC_4H_9$ and —$CH_2OH$

The organic polymer is typically supplied or prepared as a concentrated solution, in some embodiments in a hydrophilic solvent. Suitable hydrophilic solvents include water and oxygenated solvents, such as alcohols, ethers, ketones and esters. Example solvents include $C_{1-6}$ alcohols such as methanol, ethanol, propanol, isopropanol, butan-1-ol, butan-2-ol, pentan-1-ol and hexan-1-ol, of which ethanol is particular.

The primer layer according to the present technology also includes a porous particulate material. The porous particulate material acts as a filler and further aids in the absorption of the humectant organic solvents (particularly the non-volatile components thereof) contained in the conductive liquid. The porous particulate material also serves to regulate the flow of the primer layer when dispensed into a microfluidic channel. Undesirable effects such as overflow of the primer into neighbouring regions on the fluidic device can be controlled by the appropriate choice and concentration of the porous particulate material.

In some embodiments, the porous particulate material comprises a molecular sieve. In this specification the term "molecular sieve" means a material containing pores of a precise and uniform size and which are capable of acting as an adsorbent for gases and liquids. Molecules small enough to pass through the pores are adsorbed while larger molecules, specifically metallic particles present in a conductive liquid jet ink, are not. Typically, the pore volume ranges from 0.20 to 1.20 ml/g, or in some embodiments from 0.40 to 0.60 ml/g.

Examples of suitable porous particulate materials include metal and semimetal oxides such as silica (especially amorphous silica), aluminas (including boehmite, aluminium oxide monohydrate and Bayerite, aluminium oxide trihydrate), titania, zeolites (porous aluminosilicate materials), barium sulphate and silica-alumina hydrates and oxides.

In one embodiment, the porous particulate material is alumina boehmite, AlO(OH). Particularly suitable alumina boehmites include the range of water dispersible alumina boehmites available as DISPERAL® and DISPAL® from Sasol.

The alumina may be an organically modified alumina. In particular, when the alumina is alumina boehmite, the hydroxyl group on the boehmite may be etherified by substitution of the hydrogen with an alkyl group, or esterified by substitution of the hydrogen with an acyl group, which may be a carboxyl or sulfonyl group. Examples of suitable alumina-modifying reagents for forming include alkylating agents, such as alkyl halides or sulfonates, acylating agents, such as carboxylic acid chlorides and carboxylic acid anhydrides, and sulfonylating agents, such as sulfonic acids, sulfonic acid chlorides and sulfonic acid anhydrides. A particular modifying reagent is p-toluenesulfonic acid.

In another embodiment, the porous particulate material is silica, especially fumed silica.

In another embodiment, the porous particulate material is a zeolite. Zeolites are porous aluminosilicate materials capable of acting as molecular sieves. Zeolites have a porous structure that can accommodate a wide variety of cations, such as $Na^+$, $K^+$, $Ca^{2+}$, and $Mg^{2+}$. These positive ions can readily be exchanged for others in a contact solution. Examples of suitable zeolites include amicite, analcime, barrerite, bellbergite, bikitaite, boggsite, brewsterite, chabazite, clinoptilolite, cowlesite, dachiardite, edingtonite, epistilbite, erionite, faujasite, ferrierite, garronite, gismondine, gmelinite, gobbinsite, gonnardite, goosecreekite, harmotome, herschelite, heulandite, laumontite, levyne, maricopaite, mazzite, merlinoite, mesolite, montesommaite, mordenite, natrolite, offretite, paranatrolite, paulingite, pentasil (also known as ZSM-5), perlialite, phillipsite, pollucite, scolecite, sodium dachiardite, stellerite, stilbite, tetranatrolite, thomsonite, tschernichite, wairakite, wellsite, wilihendersonite and yugawaralite.

The porous particulate material is typically present as a dispersion in a solvent. Typically, the solvent is water or a hydrophilic organic solvent such as an alcohol, an ether (particularly a glycol ether such as those described and exemplified below), a ketone or an ester. In some embodiments, the solvent in which the porous particulate material is dispersed is water.

In one embodiment, the primer layer comprises an organic polymer, as defined above, in which the porous particulate material is dispersed. However, it has also been found according to this technology that the porous particulate material may be effective as a primer layer even in the absence of an organic polymer. Therefore, in an alternative embodiment the primer layer consists essentially of a porous particulate material, as defined and exemplified above (either in its broadest aspect or a more restricted aspect) dispersed in a solvent as defined and exemplified above (either in its broadest aspect or a more restricted aspect).

In some embodiments, particularly those embodiments where the primer layer comprises an organic polymer in which a porous particulate material is dispersed, the primer layer contains at least 70%, in some embodiments at least 75%, in some embodiments at least 80%, in some embodiments at least 85%, and in some embodiments at least 90% by weight of the porous particulate material (as a percentage by weight of the concentrated primer, before dissolution in the solvent).

In some embodiments, particularly those embodiments where the primer layer comprises a porous particulate material without an organic polymer, the primer layer contains up to 50%, in some embodiments up to 40%, in some embodiments up to 30%, in some embodiments up to 25%, and in some embodiments up to 20% by weight of the porous particulate material (as a percentage by weight of the concentrated particulate material in the primer, the remainder comprising the solvent).

The primer layer is generally applied to the substrate diluted in solution, in some embodiments in a hydrophilic/hydrophobic solvent. The solvent used to dilute the primer layer should in some embodiments exhibit a lower surface tension with respect to surface energy of the microfluidic substrate. The surfactant-like properties of the solvent, low surface tension and slow evaporation rate enables the formulated primer layer to flow across the region of the substrate only where it is intended to be applied. Suitable solvents include oxygenated solvents, such as alcohols, and ethers (particularly glycol ethers such as those defined and exemplified below), ketones and esters.

In some embodiments, the solvent in which the primer layer is diluted is a glycol ether. These solvents exhibit a good range of properties such as good solvency of hydrophilic and hydrophobic coating polymers, good flow behaviour on hydrophobic surfaces and controllable evaporation (drying). Examples of suitable glycol ethers include: ethylene glycol mono($C_{1-6}$)alkyl ethers such as ethylene glycol monopropyl ether, ethylene glycol monoisopropyl ether (isopropoxyethanol) and ethylene glycol monobutyl ether; ethylene glycol phenyl ether; diethylene glycol mono($C_{1-6}$) alkyl ethers such as diethylene glycol monomethyl ether, diethylene glycol monoethyl ether (CARBITOL™), diethylene glycol monobutyl ether and diethylene glycol monohexyl ether; triethylene glycol mono($C_{1-6}$)alkyl ethers (alkoxytriglycols) such as triethylene glycol monomethyl ether (methoxytriglycol), triethylene glycol monoethyl ether (ethoxytriglycol) and triethylene glycol monobutyl ether (butoxytriglycol); propylene glycol ($C_{1-6}$)alkyl ethers such as propylene glycol methyl ether, propylene glycol n-propyl ether, propylene glycol n-butyl ether; propylene glycol phenyl ether; dipropylene glycol mono($C_{1-6}$)alkyl ethers such as dipropylene glycol monomethyl ether, dipropylene glycol mono(n-propyl)ether and dipropylene glycol mono(n-butyl) ether, and tripropylene glycol mono($C_{1-6}$)alkyl ethers such as tripropylene glycol monomethyl ether and tripropylene glycol mono(n-butyl)ether.

Particular examples are ethylene glycol monoisopropyl ether (isopropoxyethanol), dipropylene glycol monomethyl ether, and mixtures thereof.

In some embodiments, the primer layer is applied in a solution containing 50 to 95%, in some embodiments 60 to 90%, in some embodiments 65 to 80%, by weight of the concentrated primer layer and 5 to 50%, in some embodiments 10 to 40%, in some embodiments 20 to 35%, by weight of the diluting solvent.

Conductive Material

The devices of the present technology further comprise an electrically conductive pattern over the primer layer. In the method of the present technology, step (c) comprises applying a conductive liquid over the primer layer and step (d) comprises allowing the conductive liquid to flow throughout the microfluidic channel by capillary action to form the planar electrode structure.

In some embodiments, the surface tension of the conductive liquid is lower than the surface energy of the receptive substrate. In some embodiments, the properties of the conductive liquid should be such that it does not dry before complete coverage of the substrate is attained by fluid flow. Either or both (for example, both) of these properties assist in achieving complete fluidic flow, and therefore complete and homogeneous coverage of the channels with the conductive liquid.

The conductive liquid comprises electrically conductive particles dispersed in a carrier medium. In some embodiments, the electrically conductive material from which the particles are formed is a metal. The metal is not particularly limited provided it does not react with the solvents. Examples of suitable metals include alkaline earth metals such as beryllium, magnesium, calcium, strontium and barium; transition metals such as zinc, molybdenum, cadmium, scandium, titanium, vanadium, chromium, manganese, iron, cobalt, nickel, copper, yttrium, zirconium, niobium, technetium, ruthenium, rhodium, palladium, silver, hafnium, tantalum, tungsten, rhenium, osmium, iridium, platinum and gold; and p-block metals such as aluminium, gallium, indium, tin, thallium, lead and bismuth. Example metals include nickel, copper, palladium, tungsten, cadmium, silver, platinum and gold. A particular example is silver.

It will be understood that the alloys or mixtures of two or more of the above-mentioned metals and other conductive compounds may be used.

In a further alternative embodiment, the conductive material is a conductive metal oxide. These materials are metal oxides doped with another metal in sufficient amounts to cause the material to be electrically conductive. Examples of conductive metal oxides include indium tin oxide (ITO), antimony tin oxide, indium-doped cadmium oxide and aluminium-doped zinc oxide.

In an alternative embodiment, the conductive material is a conductive form of carbon. Examples of conductive forms of carbon include graphite and carbon nanotubes.

In some embodiments, the metallic or electrically conductive particles dispersed in the conductive liquid are nanoparticles. The particle size of the nanoparticles should be such that they are not absorbed into the primer layer. Typically, the particle size of the nanoparticles ranges from 5 to 200 nm, in some embodiments 50 to 150 nm.

In the conductive liquid used in the present technology, the conductive particles are dispersed in a carrier medium. The carrier medium includes a solvent. The solvent is not particularly critical provided that it permits the formation of a stable suspension of the conductive particles and can permits the conductive liquid to flow throughout the microfluidic channel by capillary action to form the planar electrode structure.

In some embodiments, the carrier medium additionally contains water.

In some embodiments, the solvent is an organic solvent, particularly a water-miscible organic solvent.

In some embodiments, the solvent has a surface tension and/or a boiling point which is particularly suited to facilitate fluidic flow of the suspension into the microfluidic channels. Typically, the solvent has a boiling point in the range of 80 to 300° C., in some embodiments 100 to 200° C. Typically, the solvent has a surface tension in the range of 10 to 45 mN/m, in some embodiments 20 to 40 mN/m.

In the conductive liquids used in the present technology, the conductive particles are dispersed in a carrier, which includes a solvent. Suitable classes of solvents include oxygenated solvents, such as alcohols (particularly polyols, i.e. alcohols containing more than one OH group), ethers, ketones and esters. Particular examples of solvents include:

$C_{3-10}$ monoalcohols, such as 1-propanol, 2-propanol, 1-butanol, 2-butanol, isobutanol, t-butanol, 1-pentanol, 2-pentanol, 1-hexanol, 2-hexanol, 4-methyl-2-pentanol, 1-heptanol, 2-heptanol, 1-octanol, 2-octanol, 1-nonanol, 2-nonanol, 1-decanol and 2-decanol;

$C_{2-8}$ diols such as ethylene glycol, propylene glycol, 1,3-butanediol, 1,4-butanediol, 1,2-pentanediol, 1,5-pentanediol, 1,6-hexanediol, diethylene glycol, triethylene glycol, 1,3-cyclohexanedimethanol and 1,4-cyclohexanedimethanol, $C_{3-6}$ triols such as glycerol or trimethylolpropane;

mono esters containing a total of 5 to 10 carbon atoms, particularly $C_{3-8}$ alkyl acetates such as propyl acetate, butyl acetate, isopropyl acetate, n-pentyl acetate, n-hexyl acetate, n-heptyl acetate and n-octyl acetate, $C_{2-6}$ alkyl propanoates such as ethyl propanoate, propyl propanoate, butyl propanoate and pentyl propanoate;

glycol ethers, as defined and exemplified above in relation to the primer layer, such as dipropylene glycol methyl ether or isopropoxyethanol;

glycol esters, particularly glycol acetates, such as ethylene glycol acetate, ethylene glycol propanoate, ethylene glycol butanoate, ethylene glycol diacetate, propylene glycol diacetate, 1,3-butanediol diacetate, 1,4-butanediol diacetate, and glycol ether diacetates such as ethylene glycol n-butyl ether acetate, diethylene glycol n-butyl ether acetate, propylene glycol methyl ether acetate and dipropylene glycol methyl ether acetate.

In one embodiment, the solvent is ethylene glycol diacetate, which has a surface tension of 33 mN/m which is particularly suited to aiding capillary flow.

In another embodiment, the solvent is a mixture of water and dipropylene glycol monomethyl ether. In this embodiment, the water and dipropylene glycol monomethyl ether are typically present in a mixing ratio of 10:90 to 90:10 by volume, in some embodiments 30:70 to 70:30 by volume. In one embodiment, the solvent is a 50:50 (by volume) mixture of water and dipropylene glycol monomethyl ether, which has a surface tension of 33 mN/m which is particularly suited to aiding capillary flow.

A wide range of conductive liquids are commercially available from a number of sources. Examples of suitable conductive liquids are those available from Sun Chemical Corporation commercially available under the trade names EMD5603 and EMD5714.

The conductive liquid may optionally further include a corrosion inhibitor. Such corrosion inhibitors are required when the metal is non-noble (i.e. a metal other than ruthenium, rhodium, palladium, silver, osmium, iridium, platinum or gold) to prevent oxidation of the metal. Examples of corrosion inhibitors include hydrazine, amines such as hexamine, phenylenediamine or dimethylethanolamine or sterically hindered amines such as those described and exemplified below; quaternised amines, polyamines such as polyaniline; aldehydes such as cinnamaldehyde; imines; and inorganic corrosion inhibitors such as nitrites (eg sodium nitrite), chromates and phosphates; and mixtures of any thereof.

In some embodiments, the corrosion inhibitor is a sterically hindered amine. Suitable hindered amines include diethanolamine, triethanolamine, imidazole derivatives and their salts with polycarboxylic acids. Particularly suitable corrosion inhibitors are commercially available from BASF Corporation under the trade names Corrosion Inhibitor Amine O, Irgacor L184, and Irgacor L190 Plus. These are particularly suitable because of their solubility in hydrophilic formulations.

In some embodiments, the carrier medium also includes a polymer, typically an organic polymer. The physical and chemical properties of the polymer should be such that the conductive material can be reliably deposited onto the primer layer by methods such as inkjet printing. In some embodiments, the average molecular weight ($M_w$) of the polymer is lower than 100,000, in some embodiments from 5,000 to 50,000.

In some embodiments, the viscosity of the polymer may range from 5 to 20 mPa·s, in some embodiments 9 to 15 mPa·s.

However, when alternative methods such as hot melt printing are used to deposit the conductive material, polymers of much higher viscosity (up to 1 Pa·s) may be used.

Examples of polymers suitable for including in the carrier medium include:

(1) Acrylic polymers, i.e. a polymer comprising acrylic or methacrylic repeating units (as defined and exemplified above, either in its broadest aspect or a more restricted aspect), and mixtures thereof. The acrylic polymer may be a homopolymer (i.e. a polymer consisting only of one type of acrylic or methacrylic repeating unit) or a copolymer (i.e. a polymer comprising one or more other repeating units in addition to the acrylic or methacrylic repeating unit; the additional repeating unit may be any of the vinyl repeating units defined and exemplified above). Suitable examples include poly (methyl acrylate), poly (methyl methacrylate), poly (butyl acrylate), poly(butyl methacrylate), copolymers thereof, and mixtures of the above homopolymers and copolymers. A particular acrylic polymer (e.g. methyl methacrylate-butyl methacrylate copolymer) available as Neocryl 890 from DSM NeoResins.

(2) Epoxy resins, such as those defined and exemplified above in relation to the epoxy resin portion of the glass-reinforced epoxy laminate substrate, and mixtures thereof.

(3) Polyurethanes and mixtures thereof. Polyurethanes are polymers produced by the polyaddition reaction of a polyisocyanate, i.e. a molecule with two or more isocyanate (—NCO) functional groups, with a polyol (as defined and exemplified above in relation to epoxy resins), typically in the presence of a catalyst. The reaction product is a polymer containing the urethane linkage, —RNHCOOR'—.

In one embodiment, the isocyanate may be aromatic, examples of which include diphenylmethane diisocyanate or toluene diisocyanate. In another embodiment, the isocyanate may be aliphatic, such as hexamethylene diisocyanate or isophorone diisocyanate. In another embodiment, the isocyanate may be a polymeric isocyanate, for example is polymeric diphenylmethane diisocyanate, which is a blend of molecules with two-, three-, and four- or more isocyanate groups, with an average functionality of 2.7.

In one embodiment, the polyol may be a diol or triol, such as ethylene glycol, 1,4-butanediol, diethylene glycol, glycerol, or trimethylolpropane. In another embodiment, the polyol may be a polyether polyol or polyester polyol. Polyether polyols are prepolymers having ether groups in the prepolymer backbone and hydroxy groups (typically at their termini) capable of reacting with the polyisocyanates. They are typically formed by addition of propylene oxide or ethylene oxide onto a hydroxyl containing initiator (which may be a monoalcohol or a polyol, such as ethylene glycol, propylene glycol or glycerol). Polyester polyols are prepolymers having ester groups in the prepolymer backbone and hydroxy groups (typically at their termini) capable of reacting with the polyisocyanates. They are typically formed by polyesterification of a dicarboxylic acid, such as adipic acid, with a glycol, such as ethylene glycol or dipropylene glycol.

(4) Nitrocelluloses and mixtures thereof. Nitrocellulose is cellulose (as defined above) wherein some or all of the free hydroxy groups on the cellulose backbone have been nitrated to form —$ONO_2$ groups. The nitrogen content may vary from 8 to 15% by weight, in some embodiments 10.5% to 12.5% by weight.

(5) Vinylic polymers and copolymers, in particular poly (vinyl acetate), poly(vinyl chloride) and copolymers of vinyl acetate and vinyl chloride.

(6) Vinyl lactam polymers, such as those defined and exemplified above in relation to the primer layer. These are particularly suitable for those embodiments when the carrier medium additionally contains a radiation curable (especially visible light curable) monomer or prepolymer, as use of such compounds avoid aggregation of the dye/coinitiator used as a visible light initiator. This avoids unwanted photophysical effects and can lead to more efficient curing of the monomer or prepolymer.

In one embodiment, the vinyl lactam polymer is a homopolymer or copolymer including only vinyl lactam (especially polyvinyl pyrrolidone) repeating units. In another embodiment, the vinyl lactam polymer is a copolymer including an acrylic or methacrylic repeating unit (as defined and exemplified above in relation to the primer layer, particularly an alkylaminomethacrylate or alkylaminomethacrylamide repeating unit) in addition to the vinyl lactam (in some embodiments vinyl pyrrolidone) repeating unit. Particular examples are polyvinyl pyrrolidone (such as PVP K90 from ISP) and a copolymer of vinyl pyrrolidone and dimethylaminoethylmethacrylate. (such as Copolymer 958™ from ISP).

(7) Polydimethylsiloxane (PDMS), as defined and exemplified above in relation to the primer layer.

In some embodiments, the carrier medium additionally contains a radiation curable monomer or prepolymer. The nature of the radiation curable monomer or prepolymer is not especially restricted provided it contains at least one, for example more than one, unsaturated group (in some embodiments, a carbon-carbon double bond) capable of being polymerised upon exposure to suitable electromagnetic radiation (for example, ultraviolet and/or visible light). Suitable classes of radiation curable monomers or prepolymers include the following:

Polyol (meth)acrylates—these are esters of polyols with optionally substituted acrylic or methacrylic acids. In some embodiments, the polyol (meth)acrylates are acrylic or methacrylic acid esters of polyether polyols, particularly polyethylene glycol and polypropylene glycol. Particular examples include polyethylene glycol (200) diacrylate, polyethylene glycol (400) diacrylate, polyethylene glycol (400) dimethacrylate, polyethylene glycol (600) diacrylate, polyethylene glycol (600) dimethacrylate and polypropylene glycol (400) diacrylate (the numbers being the average molecular weight of the ester including the acrylate moieties).

Ethoxylated or propoxylated polyol (meth)acrylates—these are compounds derived by reacting a polyol with ethylene oxide or propylene oxide, followed by esterification of the terminal hydroxyl groups with optionally substituted acrylic or methacrylic acids. The polyol may be a diol or triol such as those described and exemplified above. The degree of ethoxylation or propoxylation (i.e. the number of moles of ethoxy or propoxy groups per mole of the starting polyol) ranges from 5 to 50, for example 10 to 30. Examples include ethoxylated (15) trimethylolpropane triacrylate and ethoxylated (20) trimethylolpropane triacrylate (the number referring to the average number of moles of ethoxy groups per mole of the starting polyol). A particular radiation curable monomer or prepolymer is the ethoxylated (20) trimethylolpropane triacrylate (available as SR415 from Sartomer) or the ethoxylated (15) trimethylolpropane triacrylate (available as CN435 from Sartomer).

The radiation curable monomer or prepolymer is generally soluble (for example, miscible) in the solvent used in the carrier medium. In some embodiments, the radiation curable monomer or prepolymer is water-soluble and/or water-dispersible.

In some embodiments, the radiation curable monomer or prepolymer is curable using visible light. Use of a visible light curable monomer or prepolymer avoids damage to the surrounding polymer compared with a solely UV-light curable monomer or prepolymer. This is particular when the conductive liquid contains metal nanoparticles, particularly silver nanoparticles.

In those embodiments wherein the conductive liquid contains a radiation curable monomer or prepolymer, a photoinitiator is also present. The photoinitiator is not particularly restricted provided that it is capable of decomposing to produce free radicals, when exposed to electromagnetic radiation (for example, visible or ultraviolet light), or is capable of reacting with another chemical species in order to produce free radicals. Examples of photoinitiators include azobis(isobutyronitrile), benzoyl peroxide, benzoin, di(tert-butyl)peroxide 2,2-dimethoxy-2-phenylacetophenone, Irgacure™ 784 and Irgacure™ 184, the structures of which are shown below.

In some embodiments, the photoinitiator comprises a visible light absorbing dye and a coinitiator is also present. The dye is capable of absorbing the visible light energy to transition to an excited state, and then reacts with the coinitiator to produce free radicals. The use of a dye and coinitiator permits curing of the radiation curable monomer or prepolymer using lower-energy visible light, which avoids undesirable damage and discolouration of the polymer.

Examples of suitable dyes include Safranin O (Basic Red 2), Eosin Y (Acid Red 87), Rose Bengal (Acid Red 94) and Acridine Orange, the structures of which are set out below:

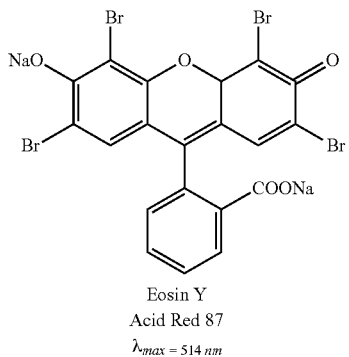

Eosin Y
Acid Red 87
$\lambda_{max} = 514\ nm$

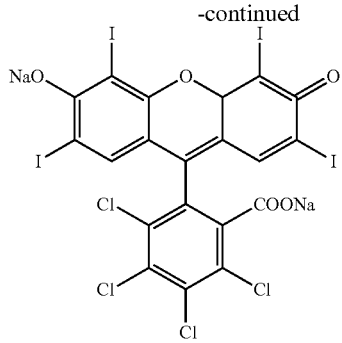

Rose Bengal
Acid Red 94
$\lambda_{max} = 548\ nm$

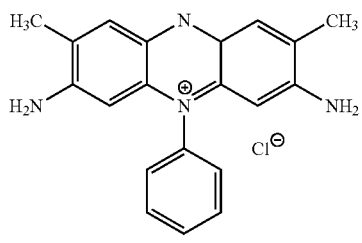

Safranin O
Basic Red 2
$\lambda_{max} = 530\ nm$

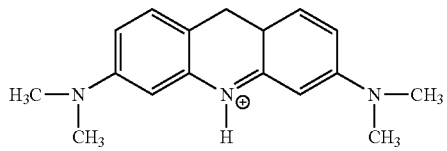

Acridine Orange
Basic Orange 14
$\lambda_{max} = 489\ nm$

Examples of suitable coinitiators include amines such as ethyl 4-dimethylaminobenzoate, ethanolamine, diethanolamine and N-methyldiethanolamine, acrylated amines of the formula:

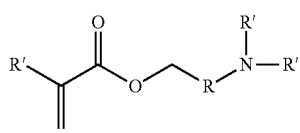

(where R=$C_{1-10}$ alkyl and R'=H or $C_{1-10}$ alkyl), and triazines of the formula:

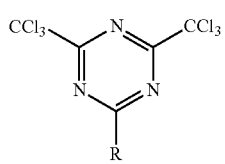

where R is selected from a group of the formula:

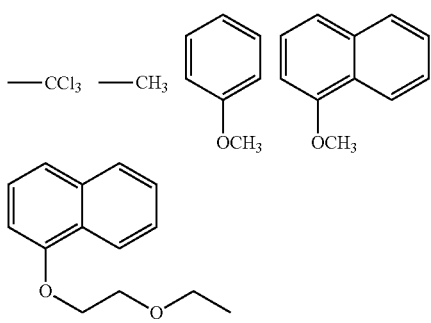

Examples of photoinitiators include Irgacure 784 and Irgacure 184, having the formula:

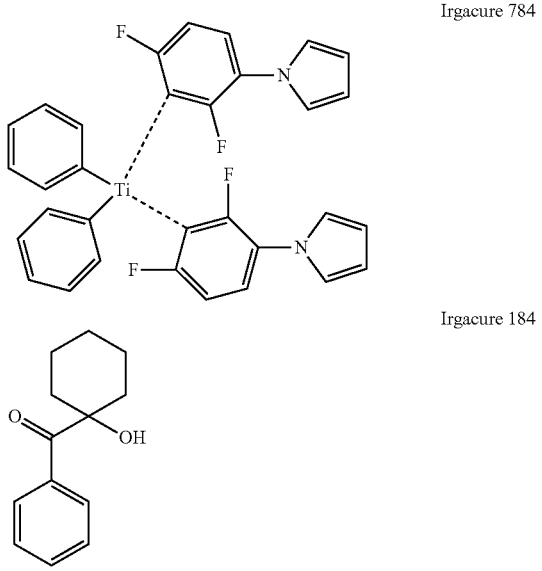

Irgacure 784

Irgacure 184

In the embodiments of the technology wherein the conductive liquid contains a radiation curable monomer or prepolymer curable using visible light, the conductive liquid may also contain a polymer. It has been surprisingly found that particular classes of polymers are able to increase the efficiency of the visible light curing. Particular are polymer classes that do not aggregate the visible light absorbing dye. The dyes represented above, especially Basic Orange 14, are particularly prone to aggregation at high concentrations—see T. Komiyama and Y. Mori, Bull. Chem. Soc. Jpn. 1976, 49, 864-867, the contents of which are incorporated herein by reference. Preventing dye aggregation, and thereby creating a more spatially diffuse dye and coinitiator distribution, facilitates more effective electron and charge transfer between the dye and coinitiator. A way of demonstrating diffusion, as opposed to aggregation, of the dye within certain polymer environments, leading to efficient dye photo decomposition, is to record the ultraviolet/visible light spectra of dyes as a function of radiation exposure and polymeric environment—the principles and results of which are further exemplified in Example 6. Examples of polymers as matrices for effective visible light curing include:

(a) Vinyl lactam polymers, such as those defined and exemplified above. Particular examples are polyvinyl pyrrolidone (such as PVP K90 from ISP) and a copolymer of vinyl pyrrolidone and dimethylaminoethylmethacrylate (such as Copolymer 958™ from ISP).

(b) Poly(vinyl alcohol) (as defined and exemplified above in relation to the primer layer).

(c) Unmodified or modified gelatin (as defined and exemplified above in relation to the primer layer).

In some embodiments, the visible light absorbing dye and coinitiator are co-located within the polymer. Co-locating the dye and coinitiator in the polymer facilitates the electron and charge transfer between the dye and the coinitiator and the generation of radicals, in a similar manner to molecules known in the art which contain dye and coinitiator moieties as part of the same molecule (see EP0341720B and K. Kawamura, Chem. Lett. 2003, 32, 1068-9, the contents of which are incorporated herein by reference).

Method of Manufacture

FIGS. 1A to 1G are schematic sections through a substrate showing in sequence steps in the manufacture of an electrode in a channel (as an example feature of a microfluidic channel structure) according to an embodiment of the technology. The process is typically carried out under cleanroom conditions. Optionally, the substrate is cleaned with a degreasing solvent (typically an isopropanol/water mixture). The substrate may be cleaned with compressed air to remove dust or contamination.

FIG. 1A shows a substrate 10 having an upper or top surface 12 and a lower or bottom surface 14. The substrate 10 has a semi-circular section channel 20 formed in the upper surface 12, e.g. by moulding (such as injection moulding), stamping, machining or etching. The channel 20 is intended to define the location of an electrode, i.e. the purpose of the channel is for it to be used in fabrication of an electrode, as opposed to use as a flow channel in the final microfluidic device. Accordingly, the channel 20, as an example of a microfluidic channel structure, is shaped to match the desired electrode structure.

Note that directional references in the present description, for example to "upper" and "lower" features, are (unless otherwise specifically indicated) merely for convenience of description and reference to the drawings, rather than implying or requiring any particular orientation of the devices in manufacture or use.

Figure 1B:
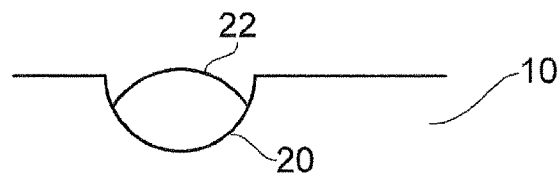

FIG. 1B shows the channel 20 in a primer distribution phase during which the channel 20 is partly filled with a solution 22 which is a primer liquid comprising a primer solvent-containing primer carrier medium. The primer solution can be applied by micro-dispensing into the channel, e.g. with a syringe, micropipette or ink jet print head nozzle. The composition of the primer solution allows it to spread along the channel by capillary action, resulting in a smooth and even coverage of the channel. Accordingly, in embodiments, the process of FIG. 1B includes waiting for the primer liquid to flow through the microfluidic channel structure by capillary action.

Figure 1C:
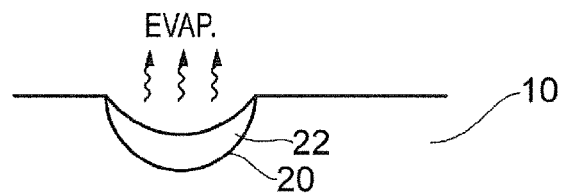

FIG. 1C schematically illustrates a primer drying phase during which the solvent evaporates to leave behind what becomes the primer layer. The composition of the primer layer may be selected to allow sufficient drying to be carried out within a reasonable time at room temperature, thereby avoiding the need for heating. Alternatively, the substrate may be held at an elevated temperature to enable or at least accelerate drying. Complete hardening of the primer may not be needed at this stage of the process, and may be deferred until the end of the electrode formation process.

Accordingly, the steps which are illustrated schematically in FIGS. 1B and 1C represent an example of the application of a primer layer to the microfluidic channel structure.

Figure 1D:
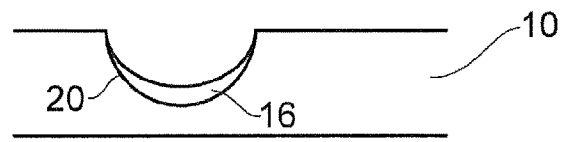

FIG. 1D schematically illustrates the component after completion of the primer drying phase. A primer layer 16 has been formed to cover substantially the entire inner surface of the channel. The primer layer is thicker at the base of the channel than in the side walls, especially near the top of the side walls where the primer layer is significantly thinner, as schematically illustrated. Depending on how the solution is applied, the uppermost side wall regions of the channel may not be covered with the primer layer.

Figure 1E:
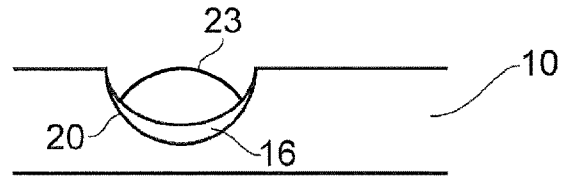

FIG. 1E shows the channel 20 during a conductive liquid distribution phase. The channel 20, already coated with the primer layer 16, is at least partly filled with a solution 23 which is a liquid comprising a solvent-containing carrier medium in which electrically conductive particles are dispersed. We refer to this liquid as the conductive liquid in reference to the fact that it contains the conductive particles which ultimately form the electrode material, not to imply that the liquid itself is electrically conductive. The conductive liquid 23 can be applied by micro-dispensing into the channel, e.g. with a syringe, micropipette or ink jet print head nozzle. The composition of the conductive liquid allows it to spread through the primer-coated channel by capillary action, resulting in a smooth and even coverage of the channel.

Accordingly, the process step shown in and described with reference to FIG. 1E provides an example of introducing a conductive liquid to the primed microfluidic channel structure, the conductive liquid comprising a carrier medium including a solvent in which electrically conductive particles are dispersed. It also represents an example of waiting for the conductive liquid to flow through the microfluidic channel structure by capillary action.

Figure 1F:
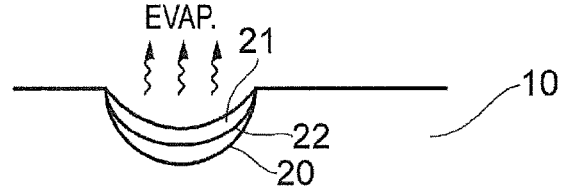
Figure 1G:
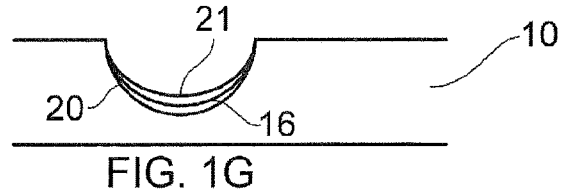

FIG. 1F schematically illustrates a conductive liquid drying phase during which the solvent of the conductive liquid, and any residual solvent in the primer layer, evaporates to leave behind what becomes the electrode layer 21. The composition of the conductive liquid may be selected to allow the drying to be carried out within a reasonable time at room temperature, thereby avoiding the need for heating. The drying step can alternatively be carried out by a number of methods known to those skilled in the art. Examples include drying in a convection oven or a hot plate, or lamp annealing (for example via an infrared lamp, a xenon lamp, or a laser such as a YAG, argon, carbon dioxide or excimer laser).

Alternatively, the substrate may be held at an elevated temperature to enable or at least accelerate drying.

In either case, the process step of FIG. 1F provides an example of evaporating the solvent from the carrier medium to allow the electrically conductive particles to form the electrode structure.

A sintering phase may follow the conductive liquid drying phase in which the conductive particles present in the ink are fused together. The sintering also removes any remaining solvent in the primer and the conductive liquid. If curing agents are present in the primer or conductive liquid solutions, this can serve to harden the electrode layer during the sintering step. The curing agents used are chosen to be slow to react, or self-crosslinking, to avoid any compositional change during distribution of the liquid in the channel by capillary flow. Where the curing agent is a polyaminoamide-epichlorohydrin curing resin the hardening occurs at neutral to alkaline pH: the hardening can therefore be accelerated by organic polymers having an amine functionality, such as a vinyl pyrrolidone-dimethylaminoethylmethacrylate copolymer (Copolymer 958).

Optionally, a separate sintering phase could be carried out for the primer layer prior to introduction of the conductive liquid 23, i.e. directly after the primer drying phase.

The electrode layer 21 can be used as an electrode layer in an active or passive microfluidic device, but may also form any other feature, for example may form part of an antenna structure. The shape of the channel need not be approximately semi-circular in cross-section as illustrated. Other shapes may be used. For example, the base and/or side walls of the channels may be flat or have flat portions. Another example is that the channels may be formed with a V-groove. Moreover, the technology is relevant not only for forming conductive features to control or sense flow in channels of microfluidic devices, but also for forming conductive features in other parts of microfluidic devices, such as reaction chambers or reagent reservoirs.

An advantage of the electrode formation process based on spreading conductive particles by suspending them in a liquid and distributing them by capillary action along a channel that has been pre-coated with a primer is that the electrode layer can be formed recessed, as illustrated, or flush with the upper surface 12 of the substrate. This means that if further layers are bonded or otherwise formed on the upper surface of the substrate, the further layer does not need to be specially shaped with recesses or distorted to accommodate the electrode layer.

The temperature of the evaporation step depends on the boiling point of the solvent. Suitable temperatures range from 50° C. to 200° C.

In some embodiments, the method of the present technology further comprises, following the evaporation step, the step of laminating the substrate with a cap layer to encapsulate or cover at least a part of the electrode structure.

The nature of the cap layer is not particularly critical to the present technology provided it is capable of adhering to the treated substrate. Examples include organic polymers such as those described and exemplified above in relation to the substrate, and inorganic polymers such as PDMS. However, for optimum adhesion it is particular that the cap layer is formed from the same material as that used to form the substrate.

The cap layer can be bonded to the substrate by a number of techniques known to those skilled in the art. Suitable techniques include solvent bonding, gluing, laser welding and thermal welding. In one embodiment, lamination of the cap layer to the substrate (for example, to cover at least a part of the electrode structure) is carried out using solvent bonding lamination. This method is particularly suitable when the substrate and cap layer are formed from the same organic polymer, especially cycloolefin copolymer. The process of solvent bonding is known to those skilled in the art and is essentially a two-step process as follows:

(1) Immersion of the substrate and cap layer in a suitable solvent in order to soften the layers; and
(2) Alignment and joining of the two parts under heat and pressure.

For step (1), the solvent is not particularly restricted provided it does not completely dissolve the substrate or cap layer. Examples include aliphatic hydrocarbons such as hexane, heptane, octane, alicyclic hydrocarbons such as cyclohexane, cycloheptane and decalin, aromatic hydrocarbons such as benzene, toluene and xylene, alcohols such as methanol, ethanol, 1-propanol, 2-propanol and 1-butanol, and mixtures thereof. A particular example is a 80:20 by volume mixture of ethanol and decalin, especially for those embodiments where the substrate and/or the cap layer are cycloolefin copolymer.

For step (2), the temperature of the press is not particularly restricted provided it is sufficient to enable the layers to join and does not cause the layers to completely melt or decompose. In one embodiment, the temperature is in the range from 40° C. to 200° C., in some embodiments 50° C. to 150° C.

For step (2), the pressure of the press is not particularly restricted provided it is sufficient to enable the layers to join and does not cause the layers to decompose. In one embodiment, the pressure is in the range from 0.2 to 10 MPa, in some embodiments 0.5 to 5 MPa.

The technique of solvent bonding is explained in more detail in T. I. Wallow et al. *Lab Chip*, 2007, 7, 1825-1831, the contents of which are incorporated herein by reference.

In those embodiments when the carrier medium contains a radiation curable monomer or prepolymer, the method of the present technology further comprises, after the lamination step, the step of applying radiation through the cap layer to cure the radiation curable monomer and thus harden the conductive liquid. The radiation may be any suitable electromagnetic radiation, but is, for example, ultraviolet or visible light.

In those embodiments when the technology includes a laminated cap layer, the substrate and/or the cap layer may be transparent to the radiation used to cure the radiation curable monomer or prepolymer.

Microfluidic Device Applications

Some functions in droplet-based microfluidics are to:
1. form, create or produce one or more droplets on demand
2. sort droplets from a series
3. route droplets at a junction
4. coalesce or fuse two droplets to a combined droplet, e.g. to initiate or terminate a reaction
5. divide or split a droplet
6. induce mixing inside a droplet
7. sense passage of a droplet, or a certain kind of droplet passing down a channel
8. analyse one or more parameters of each droplet passing a sensor
9. electrically charge a droplet, e.g. to assist its future manipulation
10. electrically neutralize (discharge) a droplet Many if not all these functions may be controlled by application or detection of electromagnetic fields, in particular electric fields, but also magnetic fields.

The coalescing function is important, since it is typically the basis under which the main activity of the device is performed. It is typical to coalesce droplets from different streams, e.g. sample and reagent, to form a coalesced droplet in which a chemical or biological reaction takes place. Such a combined droplet is sometimes referred to in the art as a nanoreactor, not just when in the nanometre scale, but even when in the micrometre scale.

Actuating or sensing electrodes may be arranged in, or to extend into, the flow channels to contact the fluid, or may be arranged outside the flow channels, adjacent thereto, so there is an insulating medium, e.g. the substrate material and/or air, between the electrode(s) and the droplet-containing carrier liquid.

The term actuating electrodes is used to refer to electrodes of an active component, whereas the term sensing electrode is used to refer to electrodes in a passive component.

For actuating electrodes, the magnitude of the electric field created in the flow channel is typically of the order of $10^6$-$10^8$ V/m.

A number of functions induced by electric field based active components are as follows:
1. charging droplets by applying an electric field via adjacent electrodes connected to a voltage source or current source
2. dividing a droplet into two droplets by inducing a dipole moment by applying an electric field via adjacent electrodes connected to a voltage source or current source which causes oppositely charged ions to move in opposed directions and therefore induces the droplet to split.
3. coalescing two droplets into one by inducing a dipole moment by applying an electric field via adjacent electrodes connected to a voltage source or current source which mutually attracts the two droplets and transiently forms a bridge through which the fusing is initiated.
4. urging or moving a droplet by an electric force induced by an applied electric field in the direction of the channel, or at least having an electric field component in the direction of the channel. This may be used to direct a droplet down a particular leg of a bifurcation, for example to sort droplets with 2 or more distinct properties, or to route a droplet stream for a period of time.
5. removing charge from droplets (neutralizing) by moving the droplets past a ground electrode arranged closely adjacent the channel or in the channel Passive components may be fabricated from conductive patterning in which electric or magnetic fields are induced by the passage of droplets (inductive loop detector). The usual range of components known from radio frequency (RF) device fabrication may be used, including inductive, resistive and capacitive elements, and combinations thereof.

A simple passive component would be an electrode pair either side of a channel connected to form a sensing circuit including the channel, wherein the resistance would be affected, typically decreased, when a droplet passes the electrode pair.

Electrically conductive patterning may be used to fabricate electromagnetic sensors to integrate with the microfluidic device, such as a Hall sensor, which for example might be useful if the droplets were associated with magnetic beads. Another sensor type which can be used for sensing the passage of droplets is an antenna structure such as a bowtie antenna.

An electrode may extend substantially at right angles to the flow channel and terminate a small distance away from the flow channel edge, or at the flow channel edge, or in the flow channel, or may extend right through the flow channel. For example, a pair of electrodes can be provided both extending substantially at right angles to each other and terminating opposed to each other on either side of the flow channel.

Other electrodes may extend in the flow channel direction and either be located in the flow channel or adjacent the flow channel. For example, a pair of electrodes may be arranged to extend parallel to a channel on either side of the channel for a section of the channel so that an electric field may be applied transverse to the flow direction over the section of the flow channel.

A wide range of droplet diameter is also envisages including the nanometre range, in particular 100-1000 nanometres, as well as 1-1000 micrometres, in particular 1-100 micrometres.

The carrier liquid may be an oil. The droplet liquid may be an aqueous solution, e.g. containing an enzyme, or an alcohol solution, or an oil solution.

Figure 2A:
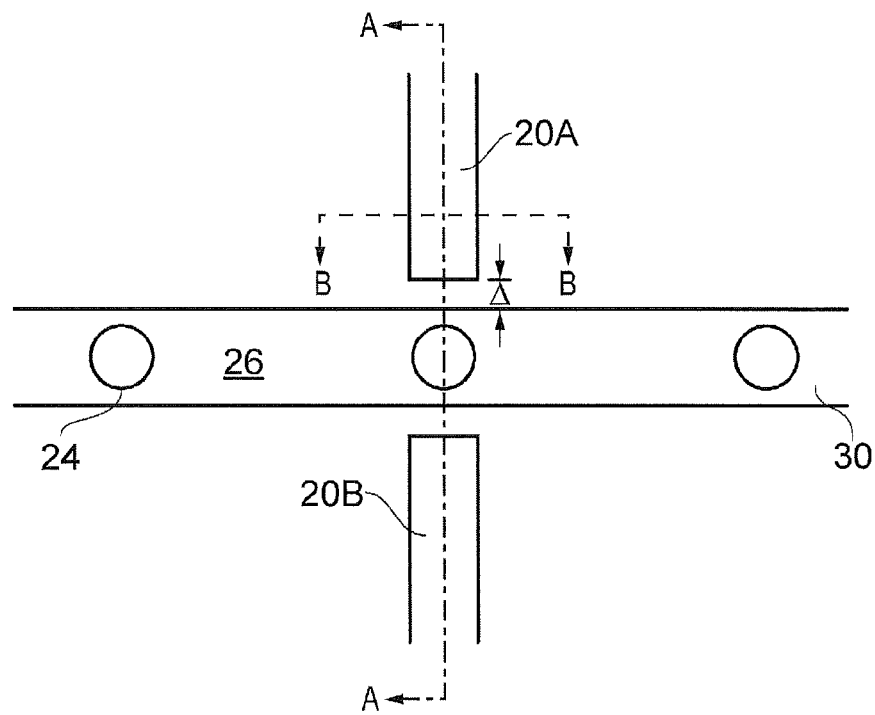
FIG. 2A is a schematic plan view of a part of a microfluidic device incorporating a pair of electrodes manufactured as shown in FIG. 1D.

FIG. 2A is a plan view of a part of a microfluidic device incorporating a pair of electrodes manufactured as shown in FIG. 1F.

A portion of a microfluidic flow channel 30 is shown in which the flow direction may be considered left to right in the drawing. The flow channel 30 is filled in use with a carrier liquid 26 in which is immiscibly suspended a series of droplets 24 of active liquid, e.g. of an analyte. A first electrode channel 20A is arranged on one side of the flow channel and extends transverse to the flow channel and terminates a distance Δ from the adjacent rim or edge of the flow channel 30. A second electrode channel 20B is arranged on the other side of the flow channel co-linear with the first electrode channel 20A and also terminates a distance Δ from its adjacent rim or edge of the flow channel 30. The first and second electrode channels 20A, 20B arranged either side of the flow channel have conductive liquid layers therein (not separately illustrated) which are formed in the manner described further above, and thereby form a pair of electrodes which can be externally actuated or sensed in order to control or sense the flow of the liquid droplets in the flow channel.

Figure 2B:
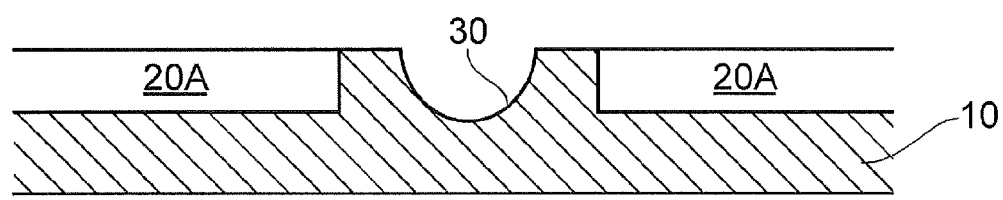
FIG. 2B is a section through line AA of FIG. 2A.

FIG. 2B is a section through the chain-dotted line AA of FIG. 2A from which the structure of the flow and electrode channels is evident.

Figure 2C:
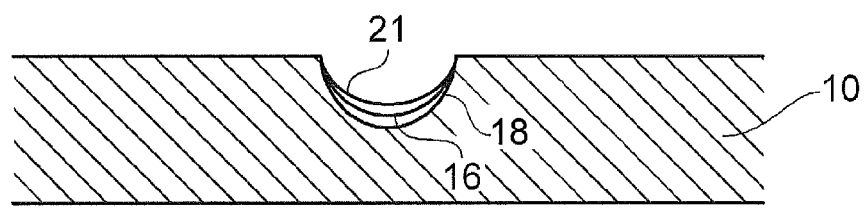
FIG. 2C is a section through line BB of FIG. 2A which is identical to FIG. 1F.

FIG. 2C is a section through dotted line BB of FIG. 2A which is identical to FIG. 1F, i.e. shows the structure of the electrode channel with primer layer 16 and electrode layer 21.

Figure 3:
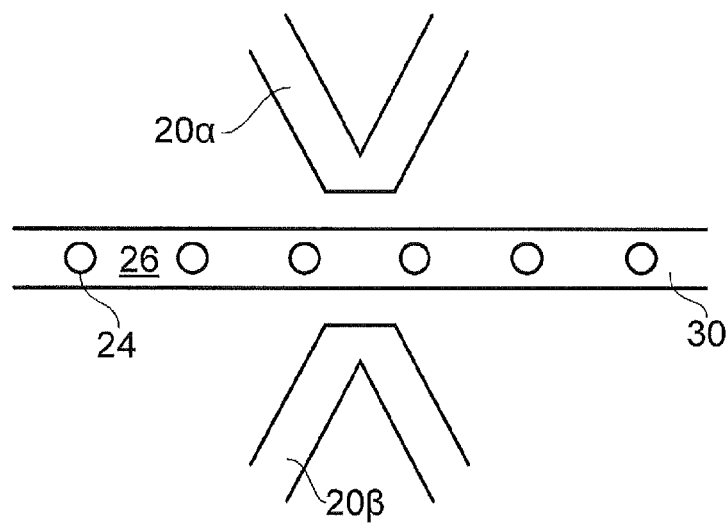
FIG. 3 is a schematic plan view of a part of a microfluidic device incorporating a pair of electrodes having an alternative topography to that of FIG. 2A.

FIG. 3 is a plan view of a part of a microfluidic device incorporating a pair of electrodes having an alternative topography to that of FIG. 2A. The electrode channels 20α, 20β have a different shape than in the example of FIG. 2A. Namely, each electrode is formed in a continuous channel portion of V-shape with the base of the V being arranged adjacent the flow channel 30.

Figure 4:
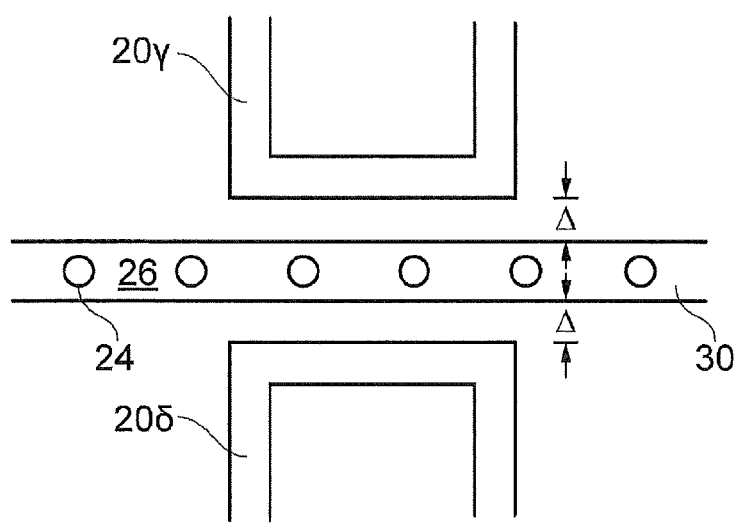
FIG. 4 is a schematic plan view of a part of a microfluidic device incorporating a pair of electrodes having an alternative topography to that of FIG. 2A.

FIG. 4 is a plan view of a part of a microfluidic device incorporating a pair of electrodes having another alternative topography. The electrodes on either side of the flow channel 20γ, 20δ are each formed from a continuous channel portion in a digital, i.e. flat-based, U-shape, so the part of the electrode that is adjacent the flow channel is defined by a portion of the electrode channel that extends parallel to the flow channel.

Other continuous channel portion shapes may also be employed. Having the part of the electrode that is adjacent the flow channel formed by a continuous channel portion has the advantage during fabrication that more even capillary flow of the conductive liquid will take place.

Figure 5:
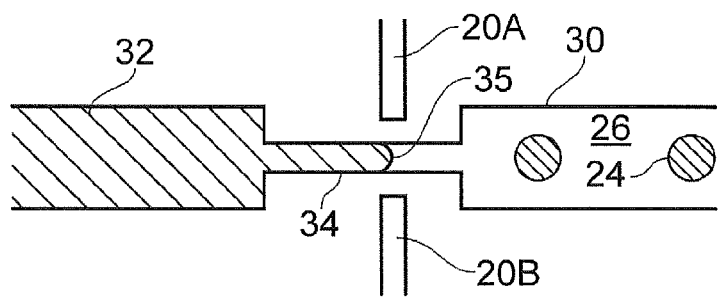
FIG. 5 is a schematic plan view of a component of a microfluidic device for generating droplets on demand.

FIG. 5 is a schematic plan view of a component of a microfluidic device for generating droplets on demand. A fluid reservoir 32 holds a volume of the active liquid (shaded) from which droplets 24 are formed. A pair of electrodes 20A, 20B are placed adjacent to a constricted channel portion 34 arranged between an outlet of the reservoir 32 and a flow channel 30. Absent actuation of the electrodes 20A, 20B the active liquid is in equilibrium with a meniscus 35 being formed in the constricted channel portion 34. When a voltage pulse is applied to the electrodes 20A, 20B, an electrophoretic force is applied to the portion of active liquid in the constricted channel portion 34, and a volume of the active liquid is broken off the contiguous reservoir volume and launched into the flow channel 30 as a droplet 24. Droplets may be produced on demand in this way, for example a series of droplets may be produced by repeatedly applying voltage pulses to the electrodes.

Figure 6:
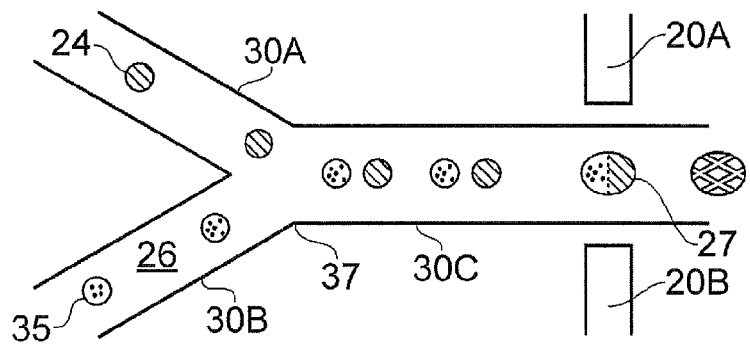
FIG. 6 is a schematic plan view of a component of a microfluidic device for coalescing pairs of droplets received from first and second channels.

FIG. 6 is a schematic plan view of a component of a microfluidic device for coalescing pairs of droplets received from first and second channels. First and second inlet flow channels 30A and 30B combine as viewed in the direction of flow at a Y-junction 37 to form a single combined flow channel 30C. A series of droplets 24 of a first active liquid (shaded) are received from the first inlet flow channel 30A. A series of droplets 25 of a second active liquid (stippled) are received from the second inlet flow channel 30B. The droplets 24, 25 are carried by a carrier liquid 26. The two series of droplets are controlled so that they arrive in adjacent pairs in the flow channel 30C, i.e. with slightly offset arrival times, as illustrated. An electrode pair 20A, 20B is arranged at a point in the flow of the flow channel 30C. The electrodes are selectively actuated with a voltage pulse at times when droplet pairs 24, 25 pass by so as to cause each droplet pair to coalesce into a combined droplet 27 (cross-hatched). The mixture of the first and second liquids may serve to activate or deactivate a chemical reaction or a biological process depending on the application.

Figure 7:
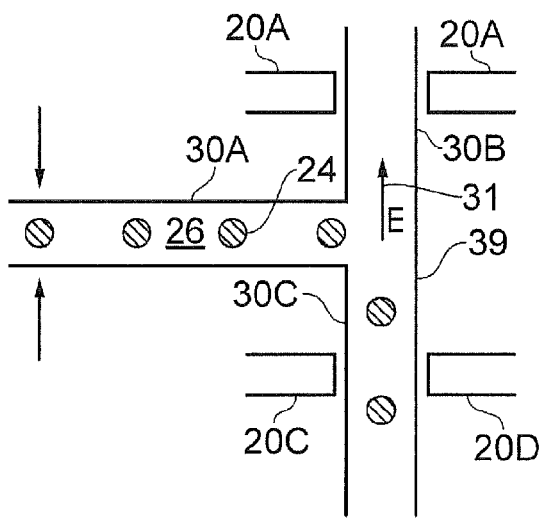
FIG. 7 is a schematic plan view of a component of a microfluidic device for routing or sorting droplets at a channel junction.

FIG. 7 is a schematic plan view of a component of a microfluidic device for routing or sorting droplets at a channel T-junction 39. A series of droplets 24 of an active liquid (shaded) carried in a carrier liquid 26 arrive along a flow channel 30A at the T-junction 39 at which the flow splits into a left flow channel 30B and a right flow channel 30C. A left electrode pair 20A, 20B is arranged part way along the left flow channel 30B and a right electrode pair 20C, 20D is arranged part way along the right flow channel 30C. The left and right electrode pairs are operated in tandem to apply an electric field either in the direction shown with the arrow 31 or the opposite direction in order to route the droplets 24 arriving along channel 30A down the left channel 30B or the right channel 30C (as illustrated). Additionally if the routing function was to be modified to be a sorting function, a sensor 38 can be arranged in the flow upstream of the T-junction, as schematically illustrated, to measure a property of each droplet on the basis of which sorting is to be performed. Individual droplets may then be directed down the left or right flow channels 30B, 30C depending on their measured properties. The sensor 38 could be an electromagnetic sensor formed with conductive liquid elements made according to the method described herein, or could be an unrelated type of sensor, such as a sensor operable to make an image-based measurement (i.e. camera or microscope with image processing) or a spectroscopic measurement.

It will be understood that further embodiments may combine the previously discussed embodiments and include conductive liquid patterning on both sides of the substrate. For example, some components, such as antennas or surface RF components such as RLC components, may be beneficially fabricated on a planar surface, i.e. typically the substrate's lower surface 14, whereas electrodes that extend into the flow channels to form conductive paths including liquid in the flow channels will need to be fabricated on the substrate's upper surface 12 where the flow channels exist.

Other Device Applications

As already mentioned, the above-described method of forming patterned conductive layers can be used outside the field of microfluidic devices to form electrode structures or other electrically conductive patterns when fabricating other kinds of device, in particular when polymer substrates are used.

FIGS. 8A to 8F are schematic views of steps in a method for fabricating a credit card format contactless smart card with embedded antenna.

Figure 8A:
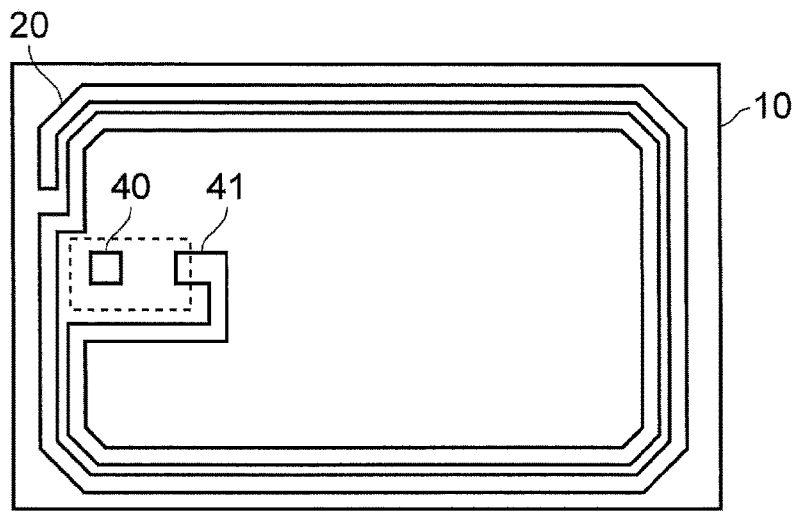
FIGS. 8A to 8F are schematic views of steps in a method for fabricating a credit card format contactless smart card with embedded antenna.

FIG. 8A is a schematic plan view of a substrate 10 for a credit card format contactless smart card with a channel 20 formed to create an antenna. The substrate 10 has an upper or top surface and a lower or bottom surface. The channel 20 is in a shape to form an antenna structure with a double coil or winding adjacent the lateral periphery of the smart card. An additional depression or pad 40 is formed which is to provide a second contact to a chip that will be embedded in the finished smart card. The first contact will formed by the adjacent end of the channel at location (pad) 41. The area to be occupied by the chip is shown with the dotted rectangle.

Figure 8B:
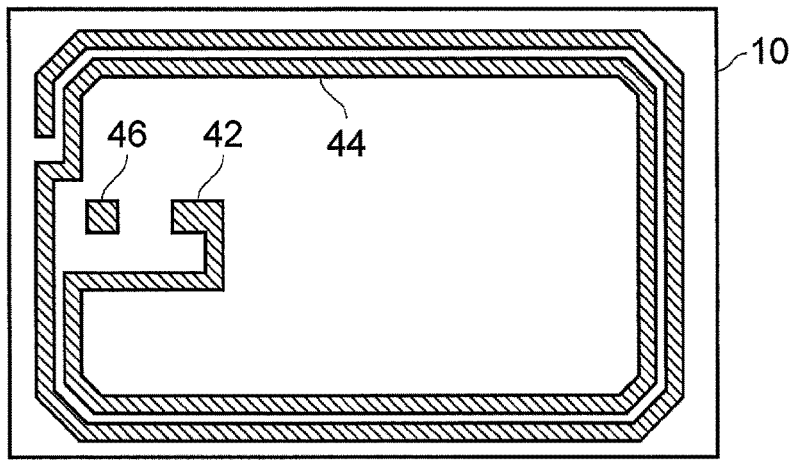

FIG. 8B shows the substrate after the channel 20 has been filled by capillary action first with a primer liquid and then with a conductive liquid in the same way as described above in connection with FIGS. 1A-1G. Namely, the two solutions can be applied by micro-dispensing into the channel 20 to form the first contact 42 and antenna structure 44 and separately to the depression 40 to form the second contact 46. The dispensing can be with a syringe, micropipette or ink jet print head nozzle. The composition of each solution allows it to be applied to the channel by capillary action, resulting in a smooth and even coverage of the channel and depression. After drying and sintering the conductive particles are fused together and form an effective electrically conducting path.

Figure 8C:
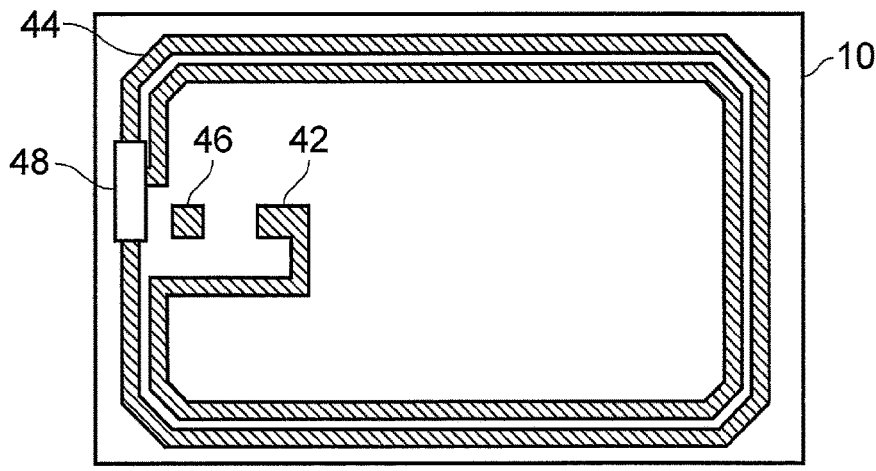

FIG. 8C schematically illustrates the next step in the process in which an insulating film 48 has been deposited, for example by vapour deposition or printing, on a local region of the antenna structure 44. Optionally, primer is printed, evaporated or otherwise deposited on top of the insulating film, the primer having similar properties to the primer liquid dispensed by capillary action in the previous step.

Figure 8D:
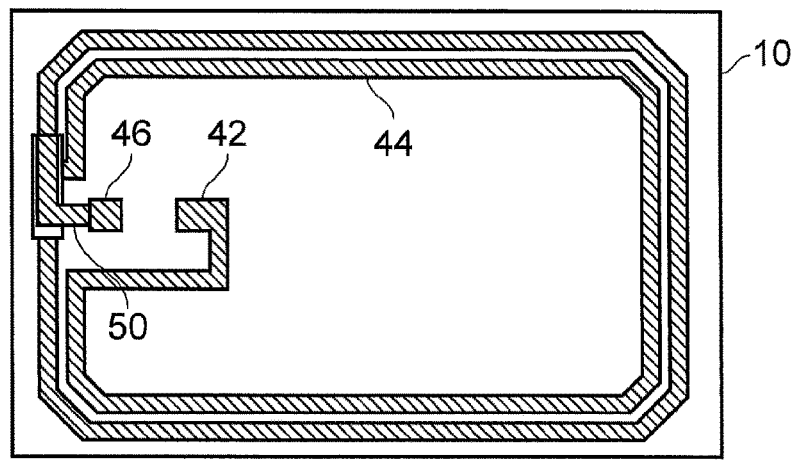

FIG. 8D schematically illustrates the next step in the process in which a conductive strip 50 is deposited, for example by vapour deposition or printing, on the insulating film 48 to connect the second contact pad 46 with the antenna so that a complete two turns of conductor are formed between the first and second contacts 42 and 46.

Figure 8E:
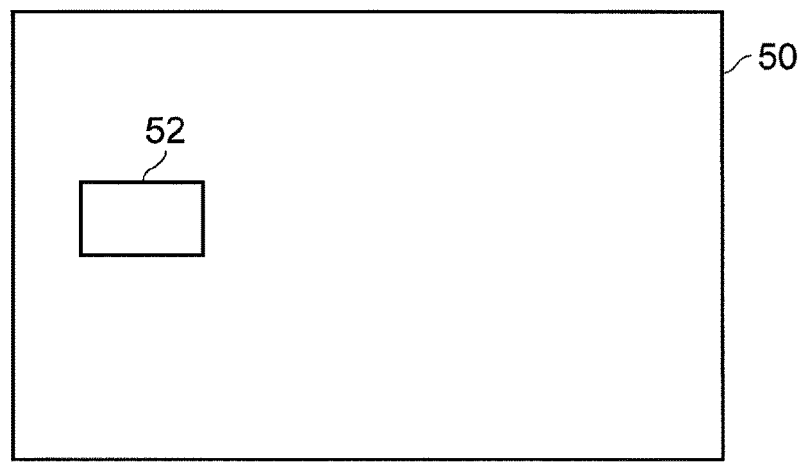

FIG. 8E schematically illustrates an intermediate layer 50 with an aperture 52 for receiving the chip.

Figure 8F:
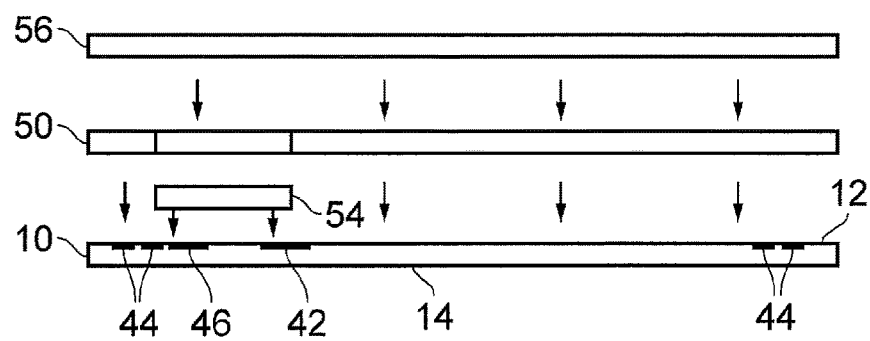

FIG. 8F shows a final assembly step in which the chip 54 is mounted on its contacts 42 and 46, the intermediate layer 50 is bonded to the upper surface 12 of the substrate 10, and a cap or laminating layer 56 is bonded to the intermediate layer 50 and substrate 10. In FIG. 8F, the lower surface of the substrate 10 is also indicated with reference numeral 14. As illustrated schematically, the antenna electrode is formed substantially flush with the upper surface 12 of the substrate, so that the intermediate layer 50 can be bonded directly onto the upper surface of the substrate 10 without needing recesses to accommodate the antenna electrodes 44 and contact pads 42 and 46 and without needing solvent-based softening to induce accommodating distortion.

The contactless smart card may for example comply with ISO 14443 or ISO 15693 for example. The chip may be an RFID (radio frequency integrated circuit) chip for example operating at a frequency of 50 MHz or 14.5 MHz. In other designs two adjacent antennas may be provided on the smart card with appropriate individual frequencies to resonate at a resonant frequency of, for example, 13.56 MHz. Referring to the above-described example, a second antenna could be formed on the underside of the laminating layer 56 using the same process as is used to form the antenna on the substrate 10.

Figure 9:
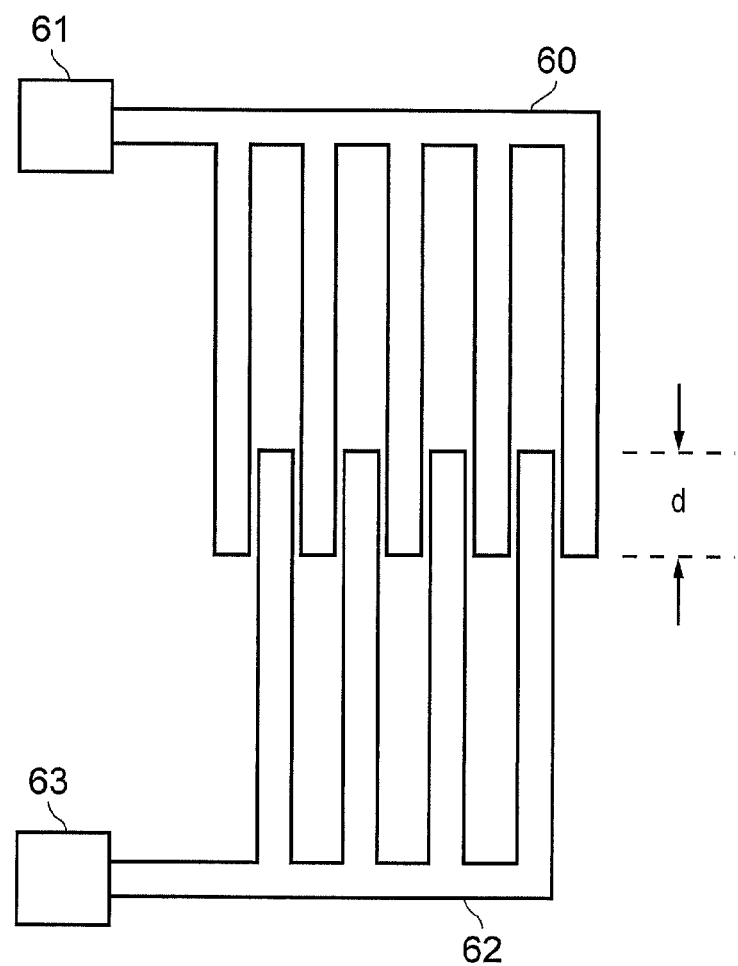
FIG. 9 is a schematic plan view of a substrate for forming a pair of interdigitated electrodes.

FIG. 9 is a schematic plan view of a substrate for forming a pair of interdigitated channels 60 and 62 to form electrodes of the same shape. The channels 60 and 62 have respective contact pad areas 61 and 63 which as well as forming suitable areas for connection to other circuit elements in a finished device, such as an electrical supply or to a sensor, provide suitable areas for deposit of primer and then conductive liquid in droplets. The respective liquid can then disperse throughout the respective channels by capillary action to form a pair of interdigitated electrodes having the pattern shown with the electrodes interdigitating over a distance d. Interdigitated electrodes are common features in different applications, including for microfluidic channels, for addressing one- and two-dimensional touch sensors, and address lines for LED and LCD displays.

It will be appreciated that channels or depressions of suitable shape can be provided for forming arbitrary shaped conductive features, including: polynomial or cloverleaf electrodes; castellated electrodes; spirals of various forms including circular, square, hexagonal and octagonal as are used to fabricate inductors in RF circuits; patterns for fabricating capacitors in RF circuits such as lateral flux capacitors formed of interdigitating electrodes and fractal capacitors based on Minkowski sausage; and the rich variety of patterns used for electrodes in touch sensors.

In some embodiments the pad width ranges from 10 µm to 1 mm, in some embodiments 100 µm to 500 µm.

In some embodiments the channel width ranges from 1 µm to 100 µm, in some embodiments 2 µm to 50 µm.

In some embodiments the channel spacing ranges from 1 µm to 100 µm, in some embodiments 2 µm to 50 µm.

In some embodiments the channel depth ranges from 1 µm to 100 µm, in some embodiments 2 µm to 50 µm.

EXAMPLES

Comparative Example 1

Conductive Liquid Flow in Untreated Polymeric Injection Moulded Devices.

Figure 10:
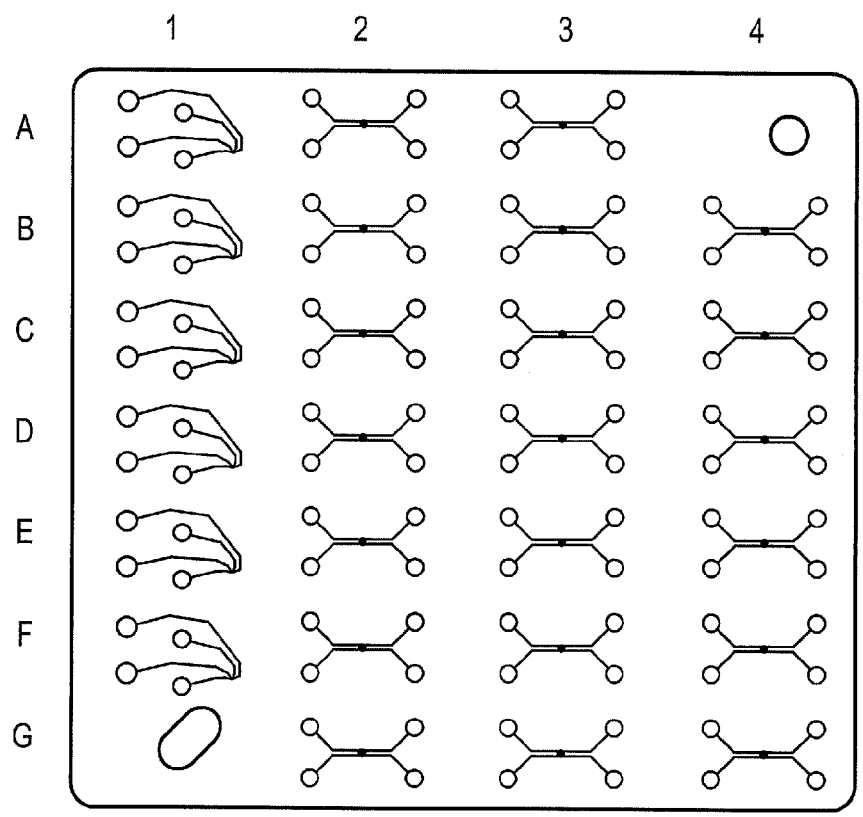
FIG. 10 shows a Schematic of Test Pattern 1 as described in Comparative Example 1.

Electrode patterns were injection moulded in cycloolefin polymer according to the structure and dimensions shown in Test Pattern 1, shown in FIG. 10. The schematic shows two types of electrode structures, each with four dispensing pads 1.60 mm in diameter. The electrode patterns vary in channel depth and width, according to Table 1. These electrode patterns were used for primer dispensing and conductive liquid tests by capillary flow in the Examples which follow.

Firstly, to gauge the effect of channel geometry on fluidic flow, two commercially available conductive liquid jet inks were dispensed only into the pads and the fluidic flow judged using a relative scale. The conductive liquid jet inks used contain silver nanoparticles, namely SunTronic EMD5603, available from SunJet Bath UK and Cabot CCI-300, available from Cabot Corporation USA.

TABLE 1

|    | Depth [µm] | Width [µm] |
|----|------------|------------|
| A1 | 155        | 13.0       |
| A2 | 155        | 13.0       |
| A3 | 170        | 13.0       |
| B1 | 155        | 18.0       |
| B2 | 155        | 18.0       |
| B3 | 150        | 18.0       |
| B4 | 155        | 18.0       |
| C1 | 160        | 24.0       |
| C2 | 155        | 24.0       |
| C3 | 125        | 24.0       |
| C4 | 130        | 24.0       |
| D1 | 160        | 30.0       |
| D2 | 150        | 30.0       |
| D3 | 110        | 30.0       |
| D4 | 110        | 30.0       |
| E1 | 155        | 36.0       |
| E2 | 155        | 36.0       |
| E3 | 90         | 36.0       |
| E4 | 95         | 36.0       |
| F1 | 155        | 42.0       |
| F2 | 160        | 42.0       |
| F3 | 70         | 42.0       |
| F4 | 70         | 42.0       |
| G2 | 155        | 48.0       |
| G3 | 55         | 48.0       |
| G4 | 50         | 48.0       |

Figure 11:
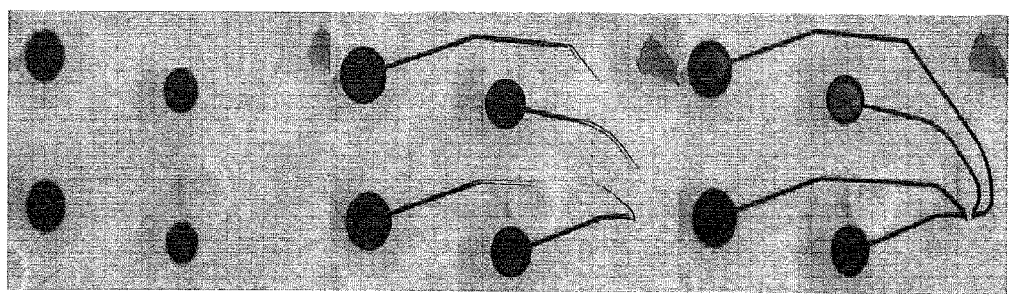
FIG. 11 shows the formation of a completed electrode pattern by capillary action, the entire pattern being filled uniformly with conductive liquid.

The flow of the conductive liquids in the preformed channels was judged for three criteria: (a) capillary flow of the fluid into the channel portion of the electrode pattern; (b) overflow of the fluid from the dispensing pad into the area surrounding the pad (an undesirable feature) and (c) formation of a complete electrode pattern by capillary action (all areas of the pattern filled uniformly with conductive liquid) as shown in FIG. 11. The results are shown in Table 2 below.

TABLE 2

| Electrode Pattern | Fluid SunTronic EMD5603 | | Fluid Cabot CCI 300 | |
|---|---|---|---|---|
| | pad | channel | pad | channel |
| A1 | OK/Overflow | no connection | OK/Overflow | no connection |
| A2 | OK/Overflow | no connection | OK/Overflow | no connection |
| A3 | OK/Overflow | no connection | OK/Overflow | no connection |
| B1 | OK/Overflow | no connection | OK/Overflow | no connection |
| B2 | OK/Overflow | no connection | OK/Overflow | no connection |
| B3 | OK/Overflow | no connection | OK/Overflow | no connection |
| B4 | OK/Overflow | no connection | OK/Overflow | no connection |
| C1 | OK/Overflow | no connection | OK/Overflow | no connection |
| C2 | OK/Overflow | no connection | OK/Overflow | no connection |
| C3 | OK/Overflow | no connection | OK/Overflow | no connection |
| C4 | OK/Overflow | no connection | OK/Overflow | no connection |
| D1 | OK/Overflow | no connection | OK/Overflow | no connection |
| D2 | OK/Overflow | no connection | OK/Overflow | no connection |
| D3 | OK/Overflow | no connection | OK/Overflow | no connection |
| D4 | OK/Overflow | no connection | OK/Overflow | no connection |
| E1 | Ok/Overflow | no connection | OK/Overflow | no connection |
| E2 | OK/Overflow | no connection | OK/Overflow | no connection |
| E3 | OK/Overflow | no connection | OK/Overflow | no connection |
| E4 | OK/Overflow | no connection | OK/Overflow | no connection |
| F1 | OK/Overflow | connection OK | OK/Overflow | no connection |
| F2 | OK/Overflow | no connection | OK/Overflow | no connection |
| F3 | OK/Overflow | no connection | OK/Overflow | no connection |
| F4 | OK/Overflow | no connection | OK/Overflow | no connection |
| G2 | OK/Overflow | connection OK | OK/Overflow | no connection |
| G3 | OK/Overflow | connection OK | OK/Overflow | no connection |
| G4 | OK/Overflow | no connection | OK/Overflow | no connection |

It can be seen in Table 2 that only on rare occasions (structures F1, G2 and G3 with the SunTronic EMD5603) are the electrodes completely filled to yield an electrical connection. The Cabot ink jet ink failed to fill the channels in all cases.

In all cases, overflow of the conductive liquid into the planar area surrounding the pad was consistently observed; the channel geometry appears to have little effect on the extent of conductive liquid flow.

Example 1

Conductive Liquid Flow in Primer Treated Polymeric Injection Moulded Devices

The same test pattern as in Comparative Example 1 was used to gauge the effect of primer treated substrate on conductive liquid flow, a direct comparison with Comparative Example 1—a test with and without primer. Three primers were made according to the present technology using the following procedure and tabulated formulations.

Copolymer 958 (a copolymer of vinyl pyrrolidone and dimethylamino-ethylmethacrylate available from ISP), supplied as 50% by weight in ethanol, was diluted to 5% concentration by stirring in additional deionised water. Dispal 14N4-80, an alumina available from Sasol GmbH, is supplied in powder form. A dispersion of Dispal 14N4-80 at 5% concentration by weight in water was made with a high speed stirrer, adjusting the pH to 3-5 with glacial acetic acid to ensure a uniform dispersion. The two preparations, now both at 5% concentration by weight, were blended together using a high speed stirrer in three ratios as defined in Table 3 (listed in the second and third column are the parts by weight of the Copolymer 958 solution to the parts by weight of the Dispal 14N4-80 dispersion). The resulting preparations are denoted in Table 3 as "Primer Conc A, B and C". Each primer concentrate was further diluted in a ratio of 1 part by weight concentrate to 4 parts by weight isopropoxyethanol as shown in column 4. The solvent addition provides the desired viscosity and surface tension for ideal fluidic flow of the primer in the electrode structures, so as to achieve uniform coverage of the primer in all areas of the test patterns. The primer was dispensed only in the pad areas of the patterns shown in FIG. 10, and allowed to flow via capillary action into all regions of the pattern.

The "coated" device was dried in a convection oven at 80° C. for 2 minutes to remove all volatile components from the primer fluid. A repeat of the test described in Comparative Example 1 was performed on the now pre-treated device using SunTronic EMD5603 together with one of Primers A, B and C; the results can be found in Table 4.

TABLE 3

| Primer Conc | 5% Copolymer 958 Content | 5% Dispal 14N4-80 Content | Solvent Dilution (primer concentrate: solvent) | Final Primer Properties | |
|---|---|---|---|---|---|
| | | | | Viscosity mPa · s | Surface Tension mN/m |
| A | 0 | 100 | 1:4 isopropoxyethanol | 9 | 26 |
| B | 10 | 90 | 1:4 isopropoxyethanol | 10 | 26 |
| C | 20 | 80 | 1:4 isopropoxyethanol | 13 | 28 |

TABLE 4

| Electrode Pattern | Primer A | | Primer B | | Primer C | |
|---|---|---|---|---|---|---|
| | pad | channel | pad | channel | pad | channel |
| A1 | OK/LO | NCX | OK/LO | NCX | OK/LO | NCX |
| A2 | OK/LO | NCX | OK/LO | NCX | OK/LO | NCX |
| A3 | OK/LO | NCX | OK/LO | CX | OK/LO | CX |
| B1 | OK/LO | NCX | OK/LO | NCX | OK/LO | CX |
| B2 | OK/LO | NCX | OK/LO | CX | OK/LO | CX |
| B3 | OK/LO | NCX | OK/LO | CX | OK/LO | CX |
| B4 | OK/LO | NCX | OK/LO | CX | OK/LO | CX |
| C1 | OK/LO | NCX | OK/LO | CX | OK/LO | NCX |
| C2 | OK/LO | NCX | OK/LO | CX | OK/LO | CX |
| C3 | OK/LO | CX | OK/LO | CX | OK/LO | CX |
| C4 | OK/LO | CX | OK/LO | CX | OK/LO | CX |
| D1 | OK/LO | CX | OK/LO | CX | OK/LO | NCX |
| D2 | OK/LO | CX | OK/LO | CX | OK/LO | CX |
| D3 | OK/LO | CX | OK/LO | CX | OK/LO | CX |
| D4 | OK/LO | CX | OK/LO | CX | OK/LO | CX |
| E1 | OK/LO | CX | OK/LO | CX | OK/LO | NCX |
| E2 | OK/LO | CX | OK/LO | CX | OK/LO | CX |
| E3 | OK/LO | CX | OK/LO | CX | OK/LO | CX |
| E4 | OK/LO | CX | OK/LO | CX | OK/LO | CX |
| F1 | OK/LO | CX | OK/LO | CX | OK/LO | NCX |
| F2 | OK/LO | CX | OK/LO | CX | OK/LO | CX |
| F3 | OK/LO | CX | OK/LO | CX | OK/LO | NCX |
| F4 | OK/LO | CX | OK/LO | NCX | OK/LO | NCX |
| G2 | OK/LO | CX | OK/LO | CX | OK/LO | CX |
| G3 | OK/LO | CX | OK/LO | NCX | OK/LO | CX |
| G4 | OK/LO | CX | OK/LO | NCX | OK/LO | CX |

Key:
OK/LO = OK/less overflow;
CX = Connection;
NCX = No connection.

It can be seen from these results Primer A is more effective for promoting conductive liquidic flow in the wider channels, whereas Primer B is more effective in the narrower channels. Primer C has broad effectiveness but its function is more sensitive to channel geometry specifics. It is clear that matching primer and channel geometry influences conductive liquidic flow, and in the majority of cases the primer has improved the fluidic flow compared to the control (the results of Comparative Example 1, shown in Table 2).

Example 2

Function of Conductive Liquid Flow Rate with Polymer Concentration in Primer To further substantiate Example 1, further tests were carried out to establish the relationship between polymer concentrations in the primer and conductive liquid flow. The primer formulations designated in FIG. 12 as "polymer Concentration 5-20 inclusive can be found in Table 5.

The test conditions were an exact repeat of those in Example 1, only the measurement criteria was changed to "ink flow rate", i.e. extent of coverage with time. The silver nanoparticle ink jet ink, SunTronic EMD5603 was once again used as a conductive liquid and dispensed on the dried primer, again on the test pattern of FIG. 10.

TABLE 5

| Polymer Concentration | 5% Copolymer 958 Content | 5% Dispal 14N4-80 Content | Solvent Dilution (primer concentrate:solvent) | Final Primer Properties | |
|---|---|---|---|---|---|
| | | | | Viscosity mPa/s | Surface Tension mN/m |
| 5 | 5 | 95 | 1:4 isopropoxyethanol | 9 | 26 |
| 10 | 10 | 90 | 1:4 isopropoxyethanol | 10 | 26 |
| 11 | 11 | 89 | 1:4 isopropoxyethanol | 10 | 26 |
| 13 | 13 | 87 | 1:4 isopropoxyethanol | 11 | 26 |
| 15 | 15 | 85 | 1:4 isopropoxyethanol | 12 | 27 |
| 20 | 20 | 80 | 1:4 isopropoxyethanol | 13 | 28 |

Figure 12:
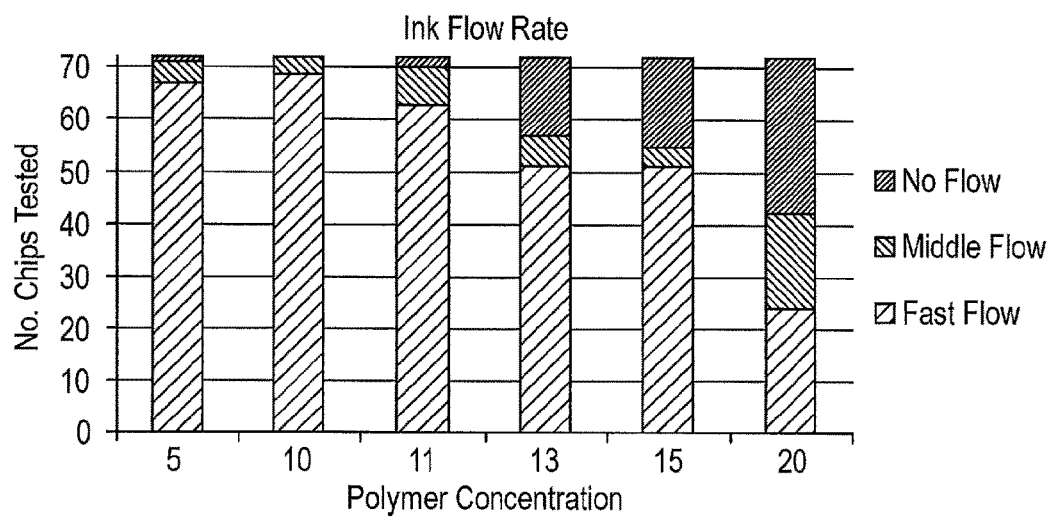
FIG. 12 is a schematic chart showing conductive liquid flow as a function of the polymer concentration in the primer of Example 1.

From FIG. 12 most notable is the decrease in flow rate of the conductive liquid as the polymer concentration is increased. Optimum flow rate is achieved at a polymer concentration of 10%. (The primer with the polymer concentration at 10% is equivalent to "Primer B" in Example 1).

It is concluded that Primer B yields the overall best result for effective channel filling with a commercial conductive liquid in the channel geometry range of 18-42 µm width and 70-150 µm depth in cycloolefin polymer.

Comparative Example 2

Conductive Liquid Flow with Polymethyl Methacrylate Substrate

Figure 13:
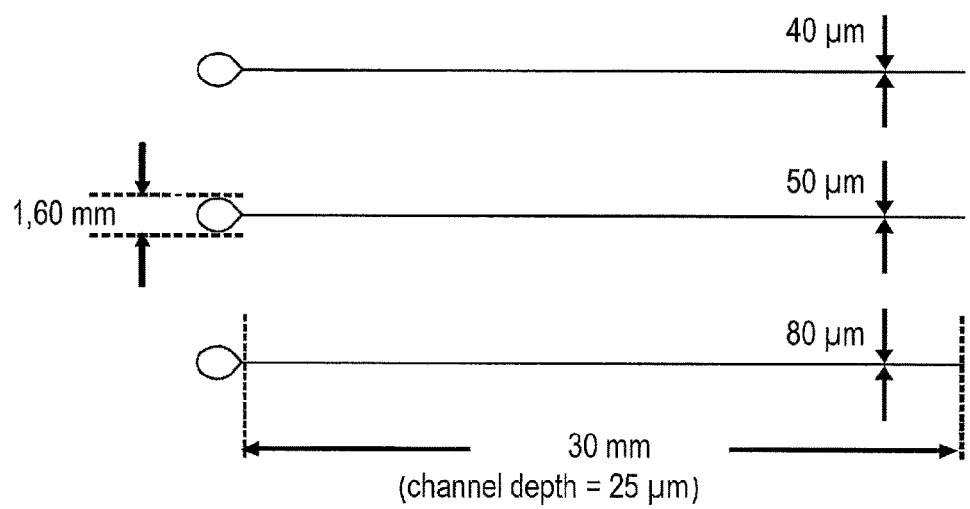
FIG. 13 schematically shows a test pattern for conductive liquidic flow in polymethyl methacrylate as described in Comparative Example 2.

The test pattern in FIG. 13 was injection moulded in polymethyl methacrylate. The fluidic flow of Suntronic EMD5603 was characterised in terms of whether the channel portions of the test design could be completely filled by capillary flow by dispensing the fluid only the pad area of the test design without primer treatment, If the channel could be completely filled, the time taken to do so was recorded.

The results are shown in Table 6.

TABLE 6

| SunTronic EMD 5603/without primer | | | |
|---|---|---|---|
| inkflow speed | | filled channel | time to be completely filled |
| 40µ channel | fastest | 100% | 11 min |
| 50µ channel | middle | 100% | 12 min |
| 60µ channel | slow | 100% | 13 min |
| 40µ channel | middle | 100% | 12 min |
| 50µ channel | slow | 100% | 13 min |
| 60µ channel | fastest | 100% | 11 min |

Figure 14:
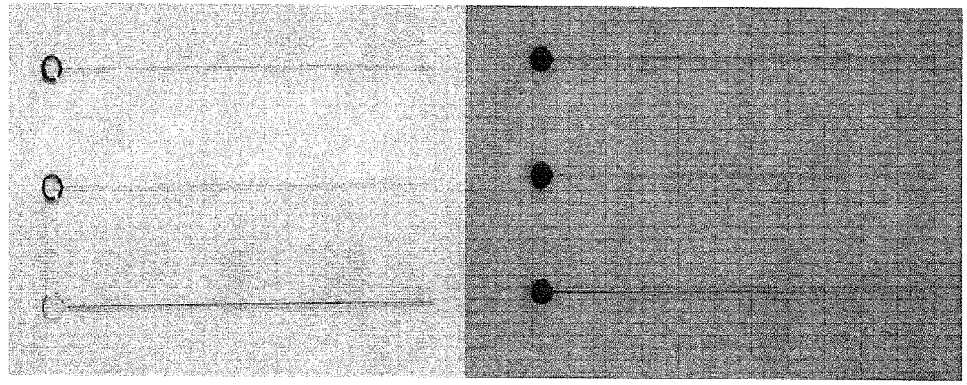
FIG. 14 schematically shows conductive liquid filling, without and with Primer B as defined in Example 1.

In all cases it was noted that the conductive liquid without primer dried heterogeneously. The fluid did not uniformly cover both pad and associated channel; and exposed uncovered areas were evident, as illustrated in FIG. 14. The problems of non-uniform coverage and irregular flow were corrected prior deposition with Primer B (as defined in Example 1).

Example 3

Conductive Liquid Flow Rate with PMMA Substrate

From Table 6 it is evident that the flow rate of conductive liquid without primer is not only irregular, but also slow. The time taken to fill a 30 mm channel is 11-13 minutes. To improve the flow speed, yet retain uniform coverage, the primer and conductive liquid compositions set out in Table 7 below can be adopted.

TABLE 7

| Primer | 10% Dispal 14N4-80 Content (aq) | 10% Dispal 25SR* Content (solvent) | Solvent Dilution (Dispal dispersion:solvent) | Final Primer Properties | |
|---|---|---|---|---|---|
| | | | | Viscosity mPa·s | Surface Tension mN/m |
| D | 100 | 0 | 1:4 isopropoxyethanol | 9 | 26 |
| E | 0 | 100 | 1:4 isopropoxyethanol | 10 | 26 |
| F | 100 | 0 | 1:4 isopropoxyethanol/ dipropylene glycol monomethyl ether | 9 | 24 |
| G | 0 | 100 | 1:4 isopropoxyethanol/ dipropylene glycol monomethyl ether | 10 | 24 |

*Alumina organically modified with p-toluenesulfonic acid

To make the primer compositions according to Table 7 required two different techniques. A dispersion of Dispal 14N4-80 at 10% concentration by weight in water was made on a high speed stirrer, adjusting the pH to 3-5 with glacial acetic acid before adding the powder to the water to ensure a uniform dispersion. The Dispal 25SR is an organically modified alumina and therefore better suited for solvent based dispersions. The technique for creating a dispersion using a high speed stirrer was also used for this material, but the 10% concentrate was made in isopropoxyethanol. Adequate dispersion of the Dispal 25SR was attained in this solvent and no glacial acetic acid was added to the dispersion, the material already comprises of formic and p-toluene sulfonic acid i.e. the organic modification. In all cases (primer concentrates D-G) the resulting 10% concentrate was further diluted with solvent to guarantee microfluidic flow. For primers labelled D and E, the primer dilution was a ratio of 1:4 Dispal dispersion to isopropoxyethanol. For primers F and G, the dilution ratio was the same, but the primers were diluted with a 50:50 blend of isopropoxyethanol and dipropylene glycol monomethyl ether, thus enabling a direct comparison of the diluents' composition.

The primers listed in Table 8 were dispensed into the pad area of the injection moulded test pattern defined in FIG. 13 and the flow rate along the connecting channel measured. The flow rate was found to be in the following order:
Primer G>Primer F>Primer E>Primer D.

It was concluded that the choice of alumina and solvent combined aids microfluidic flow and successful coverage of the microfluidic channel with primer. The organically modified alumina and isopropoxyethanol/dipropylene glycol monomethyl ether combination affording the best result. The coated channels were dried in a convection oven at 80° C. for 2 minutes to remove all volatile components prior to dispensing the conductive liquid of composition detailed in Table 9.

TABLE 9

| Chemical | Source and Product Name | Concentration (parts by weight) |
|---|---|---|
| Silver Nanopowder | Sigma Aldrich; p/n 5768323* | 25.0 |
| Ethanol (absolute) | Sigma Aldrich; p/n 32221 | 25.0 |
| Ethylene Glycol | Sigma Aldrich; p/n 102466 | 25.0 |
| Glycerol | Sigma Aldrich; p/n G7757 | 10.0 |
| Isopropoxyethanol | Sigma Aldrich; p/n 107891 | 5.0 |
| Dipropylene glycol monomethyl ether | Sigma Aldrich; p/n 484253 | 5.0 |
| Polyethylene glycol diacrylate (600)** | Sartomer Company; Sartomer 610 | 5.0 |
| Total Concentration | | 100 |

Figure 15:
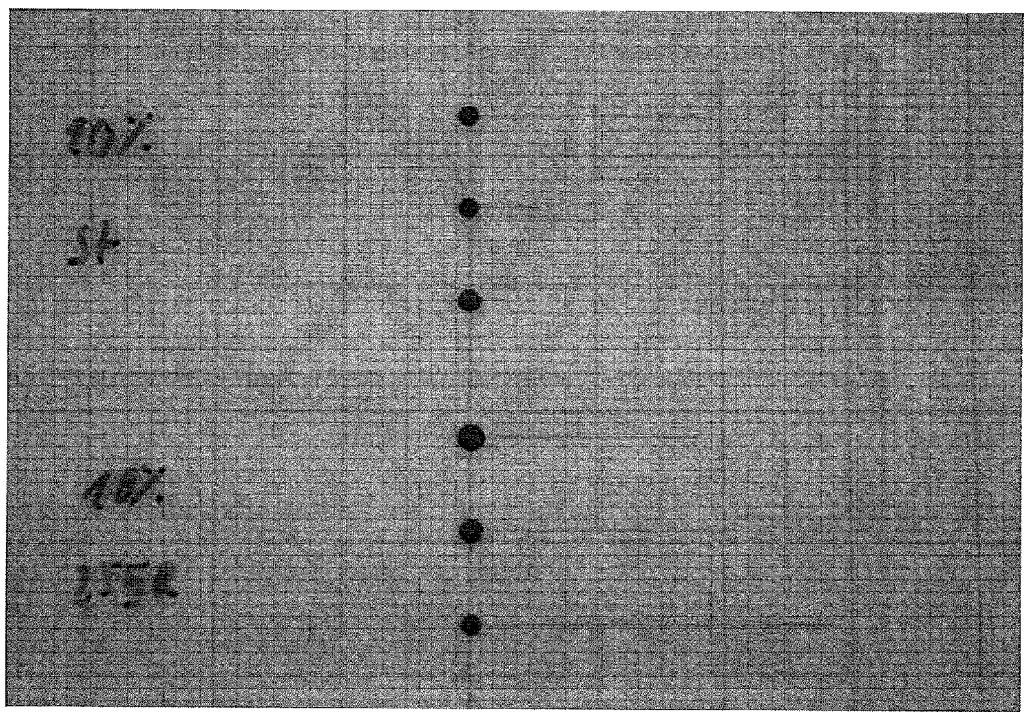
FIG. 15 schematically shows the results of Example 3 following application of the primer and conductive liquid to the injection moulded test pattern of FIG. 13.

*= silver nanoparticles (<100 nm particle size) organically treated for dispersion in polar solvents
**= hydrophilic unsaturated monomer As a reference, a non-treated pattern was dispensed with conductive liquid so as to judge the effect of the primer treated channels. The test criteria is demonstrated in FIG. 15 using primers D and E as examples, the figure illustrates how extent and rate of fluidic flow can be simply compared.

Firstly, it was noted the conductive liquid according to Table 9 without primer treatment flowed quickly and all channels were filled in approximately 1 minute. Soon after filling however, the fluid separated into two distinct phases—a silver phase and a transparent fluid phase. Ultimately, the silver did not homogeneously cover the channel, a result similar to that already described in Comparative Example 2. Conversely, uniform coverage was observed with all primers listed in Table 8 and the rate of conductive microfluidic flow was greatly improved, typically ranging from 5-30 seconds. The relative rate of conductive liquid flow was equivalent to the initial rate of primer flow i.e.
Primer G>Primer F>Primer E>Primer D.

It can only be concluded that flow rate is directly proportional to surface coverage—fast flow rate also implies effective coverage ("wetting") and dried primer composition. The organically modified alumina yielded the most effective primer for the conductive liquid containing a radiation curable component.

Example 4

Microfluidic Filling

Figure 16A:
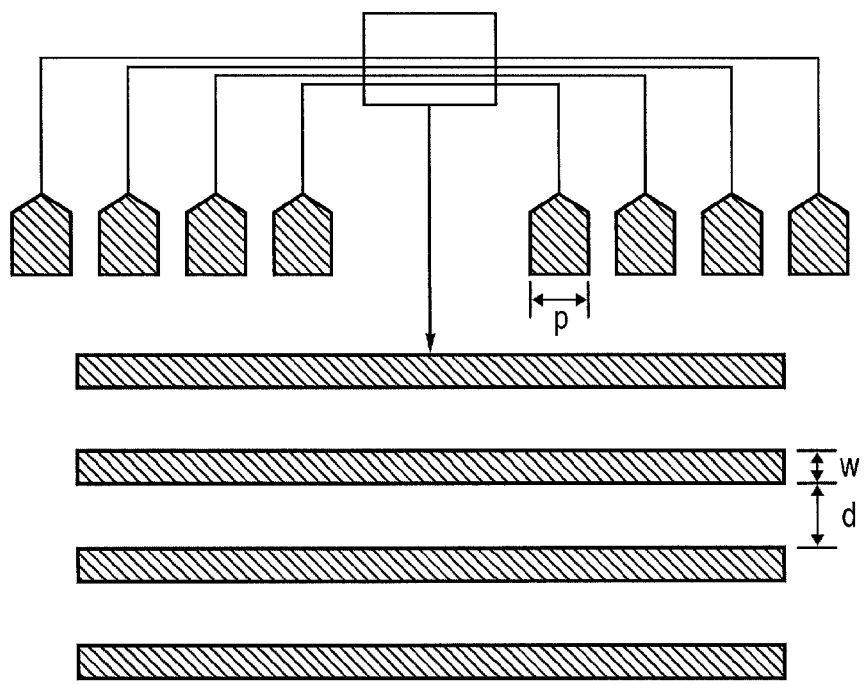
FIG. 16a schematically illustrates a test electrode pattern layout of Example 4, showing the printed area and test pattern dimensions.
Figure 16B:

The test pattern shown in FIGS. 16a and 16b was injection moulded in cycloolefin polymer. The dimensions of the test pattern are set out in Table 10.

TABLE 10

| | A | | B | | C | | D | |
|---|---|---|---|---|---|---|---|---|
| 1 | w: 10 | p: 200 | w: 10 | p: 200 | w: 5 | p: 200 | w: 10 | p: 250 |
| | d: 5 | t: 10 | d: 5 | t: 20 | d: 5 | t: 10 | d: 5 | t: 20 |
| 2 | w: 10 | p: 200 | w: 10 | p: 200 | w: 5 | p: 200 | w: 10 | p: 250 |
| | d: 10 | t: 10 | d: 10 | t: 20 | d: 10 | t: 10 | d: 10 | t: 20 |
| 3 | w: 10 | p: 200 | w: 10 | p: 200 | w: 5 | p: 200 | w: 10 | p: 250 |
| | d: 20 | t: 10 | d: 20 | t: 20 | d: 20 | t: 10 | d: 20 | t: 20 |
| 4 | w: 20 | p: 200 | w: 20 | p: 200 | w: 10 | p: 200 | w: 20 | p: 250 |
| | d: 5 | t: 10 | d: 5 | t: 20 | d: 5 | t: 5 | d: 5 | t: 20 |
| 5 | w: 20 | p: 200 | w: 20 | p: 200 | w: 10 | p: 200 | w: 20 | p: 250 |
| | d: 10 | t: 10 | d: 10 | t: 20 | d: 10 | t: 5 | d: 10 | t: 20 |
| 6 | w: 20 | p: 200 | w: 20 | p: 200 | w: 10 | p: 200 | w: 20 | p: 250 |
| | d: 20 | t: 10 | d: 20 | t: 20 | d: 20 | t: 5 | d: 20 | t: 20 |

Key:
p = pad width
w = channel width
d = channel spacing
t = channel depth

FIG. 16a depicts a test electrode pattern used to evaluate microfluidic flow on a smaller scale than in Examples 1-3 and Comparative Examples 1 and 2. The pattern has essentially eight dispensing pads connected by four channels—hence two dispensing pads per channel, one on the left of the channel and one on the right. FIG. 16b also depicts the pad area of the same electrode pattern, this area was used for dispensing and the extent of fluidic flow in the microfluidic channels was judged in the same way as explained in the previous comparative examples. Table 10 defines the dimensions of each electrode pattern tested—labelled A1 through to D6, therefore 24 test patterns in total.

As a reference, the conductive liquid, SunTronic EMD5603, was deposited into the pads by ink jet printing. Although it was partially possible to fill some channels with conductive liquid, via subsequent capillary flow from the pads to the channels, the problems of uniform coverage in the pads and channels became problematic. Dispensing larger volume of ink easily resulted in overflow from the pads, sometimes into an adjacent pad, as illustrated in Test Pattern C4. The aforementioned test pattern results are recorded in FIGS. 17a to 17c and summarised in Table 11 (corresponding to the test pattern dimensions from FIGS. 16a and 16b and Table 10).

Figure 17A:
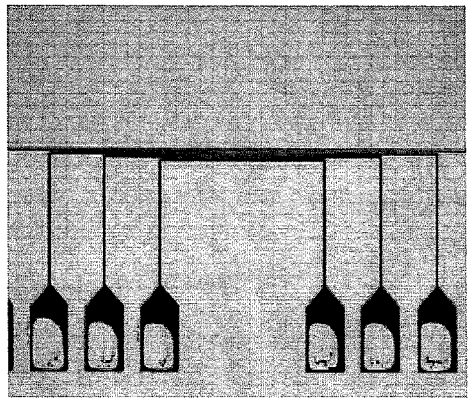
FIGS. 17a to 17c schematically illustrate the results of depositing conductive liquid by ink jet printing into pads without primer.
Figure 17B:
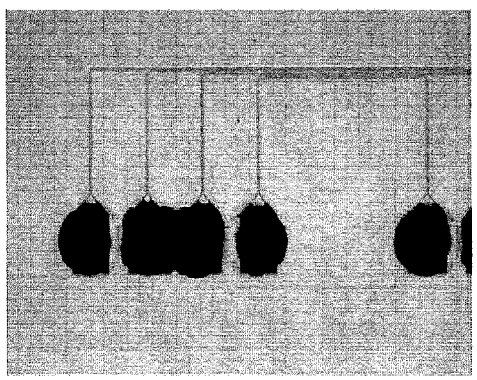
Figure 17C:
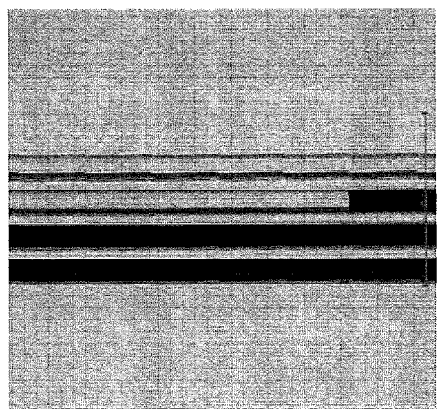

FIGS. 17a to 17c illustrate the results of depositing conductive liquid by ink jet printing into pads without primer. FIG. 17a shows Test Pattern C3 (channel width=5 μm; channel spacing=20 μm; channel depth=10 μm; FIG. 17b shows Test Pattern C4 (channel width=5 μm; channel spacing=5 μm; channel depth=5 μm) and FIG. 17c shows Test Pattern A6 (channel width=20 μm; channel spacing=20 μm; channel depth=10 μm).

TABLE 11

|   | A | B | C | D |
|---|---|---|---|---|
| 1 | N | N | N | N |
| 2 | N | N | N | N |
| 3 | N | N | N | Y |
| 4 | N | N | N | Y |
| 5 | N | N | N | Y |
| 6 | N | N | N | Y |

Key: Y = all pads and channels filled; N = pads and channels remain unfilled.

Figure 18A:
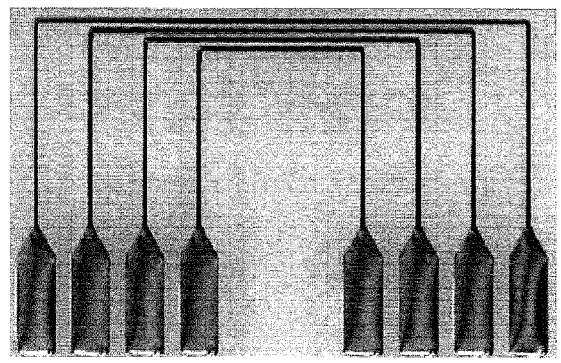
FIGS. 18a to 18d schematically illustrate test patterns filled with Primer G and conductive liquid.
Figure 18B:
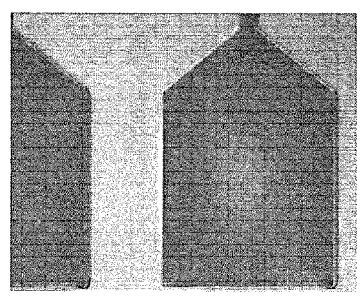
Figure 18C:
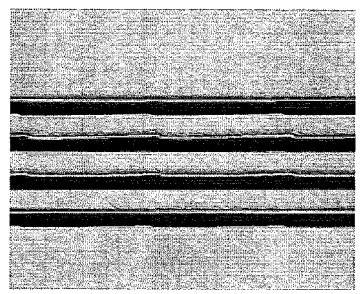
Figure 18D:
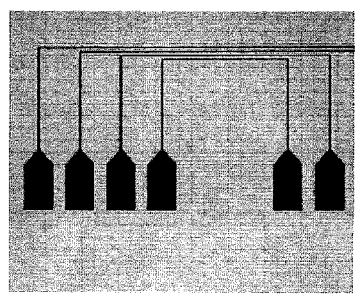

Primer G and the conductive liquid from Example 3 were deposited to the same test patterns. The results are shown in FIGS. 18a and 18b (Test Pattern C1), 18c (Test Pattern C2) and 18d (Test Pattern C3) and summarised in Table 12.

TABLE 12

|   | A | B | C | D |
|---|---|---|---|---|
| 1 | Y | Y | Y | Y |
| 2 | Y | Y | Y | Y |
| 3 | Y | Y | Y | Y |
| 4 | Y | Y | N | Y |
| 5 | Y | Y | N | Y |
| 6 | Y | Y | N | Y |

Key: Y = all pads and channels filled; N = pads and channels remain unfilled.

It is concluded that primer G and the conductive liquid according to Table 9 is a simple and effective combination for filling channel widths of at least 5 µm width and possible less. No overflow into neighbouring channels was observed. The channel geometry has an influence on successful microfluidic flow when the dimensions are in the sub 10 µm range; the summary table indicates the channel depth must at least be equal to the width.

Example 5

Use of Gold Ink

Figure 19:
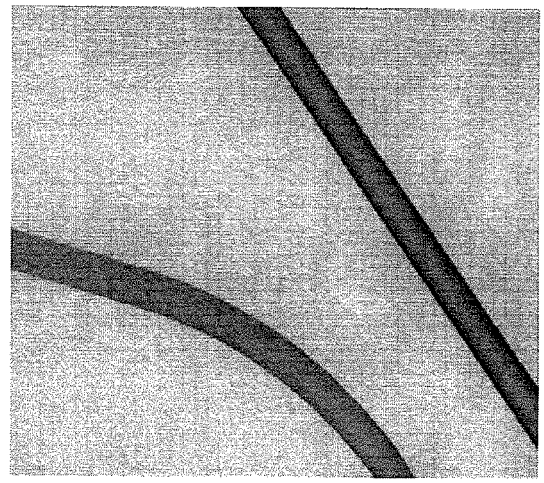
FIG. 19 schematically shows channels filled using a gold-based conductive liquid according to the present technology.

The present technology may also be carried out using gold as the metal in the conductive liquid. FIG. 19 shows gold filling according to the present technology.

Example 6

Visible Light Photoinitiator System

Metals absorb electromagnetic radiation and dispersions of metallic nanoparticles absorb selective wavelengths of radiation depending on their particle size. There is strong UV absorbance for silver nanoparticles with particle sizes of <80 nm, with a strong decrease for the same particle size distribution at around 500-550 nm. As the wavelength increases, the absorbance decreases regardless of particle size. Therefore, for metal nanoparticles (particularly silver nanoparticles) in a functional conductive liquid a curing mechanism "window" exists in the visible green to red region of the electromagnetic spectrum. To exploit this window to the full, in the embodiments of the present technology wherein the conductive liquid contains a radiation curable monomer or prepolymer, a visible light curing system may be used based on light absorbing dyes—radical producing photoinitiators that facilitate free radical polymerisation. The dye absorbs the light energy, the excited dye then undergoes energy and/or charge transfer reactions with a coinitiator. The coinitiator in turn produces the reactive radical species that initiates photopolymerisation of reactive monomers and/or prepolymers.

It is known in the art that the use of such a multi-component system is subject to photochemical and photophysical barriers that hinder efficient consecutive reactions leading to the formation of the desired reactive species. One simple factor is merely the location of the dye and coinitiator within the material to be cured. The literature suggests that linking the dye and coinitiator, so they are one molecule, has a beneficial effect on photopolymerisation—see EP0341720B and K. Kawamura, Chem. Lett. 2003, 32, 1068-9, the contents of which are incorporated herein by reference. Because these types of single molecules are not readily commercially available, in some embodiments the dye and coinitiator are located within the curing material.

It has been surprisingly found that the inclusion and selection of the dye and coinitiator within the fluid formulation can influence this property and hence also the decomposition rate of the visible light absorbing dye, leading to more effective radical generation and hence an improved degree of polymerisation.

The following example used Basic Red 2 as the dye and ethyl-4-dimethyl-aminobenzoate as the coinitiator. The following polymers were used:

Polyvinyl pyrrolidone (PVP K90™ from International Specialty Polymers)

Poly(vinyl acetate/vinyl chloride) (PVAc/VC) (E2248A™ from Wacker Chemie)

Polyvinyl pyrrolidone/dimethylaminoethylmethacrylate (Copolymer 958™ from ISP)

For the experiments, the polymers based on vinyl lactam and PVAc/VC were dissolved in solvent. Ethanol was used to dissolve the lactams and a mixture of methyl ethyl ketone and toluene was used to dissolve the PVAc/VC. The dye and coinitiator were dissolved in ethanol: the maximum solubility of Basic Red 2 in ethanol is 3% by weight and the aminobenzoate was used as a 12% solution. After complete polymer and dye dissolution the two premixes were added together to form a dyed polymer coating wherein the dye concentration is 1% based on the solid polymer. The coatings were applied by Mayer bar to polycarbonate to form a 10 µm dry film. UV/Visible spectra were taken using a Perkin Elmer Lambda 9 and the photosensitivity of the coatings was established using Hoya Ex 250 UV light source.

Figure 20:
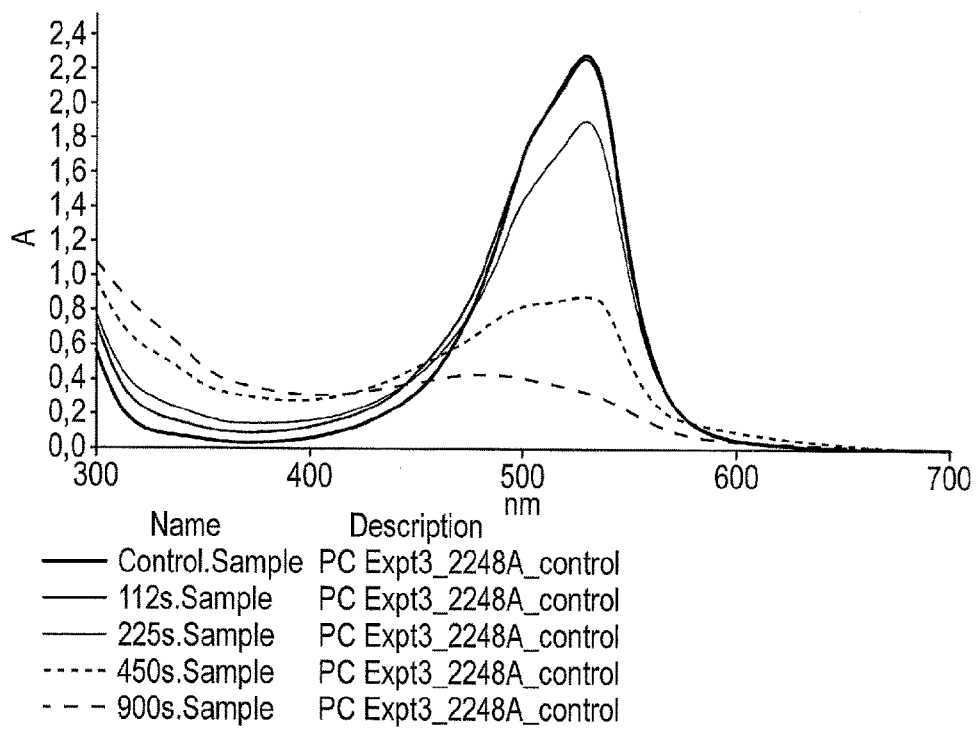
FIG. 20 schematically illustrates the UV/visible absorption spectrum of Basic Red 2 in the absence of polymers.

Initially, the absorbance and light induced decomposition of Basic Red 2 was checked. As shown in FIG. 20, it was found that the dye absorption profile is in the exact region of the green laser light emission (532 nm) and the dye is decomposed by UV exposure.

Of interest is the presence of a shoulder in the dye's absorption profile, an indication of two adsorption peaks. This shoulder is evidence of dye aggregation. When dyes aggregate, essentially the formation of dye clusters, the dye begins to adopt pigment-like properties, for example, it can become more light stable. Without wishing to be bound by theory, it is possible that dye clusters within the conductive liquid are unwanted.

Figure 21:
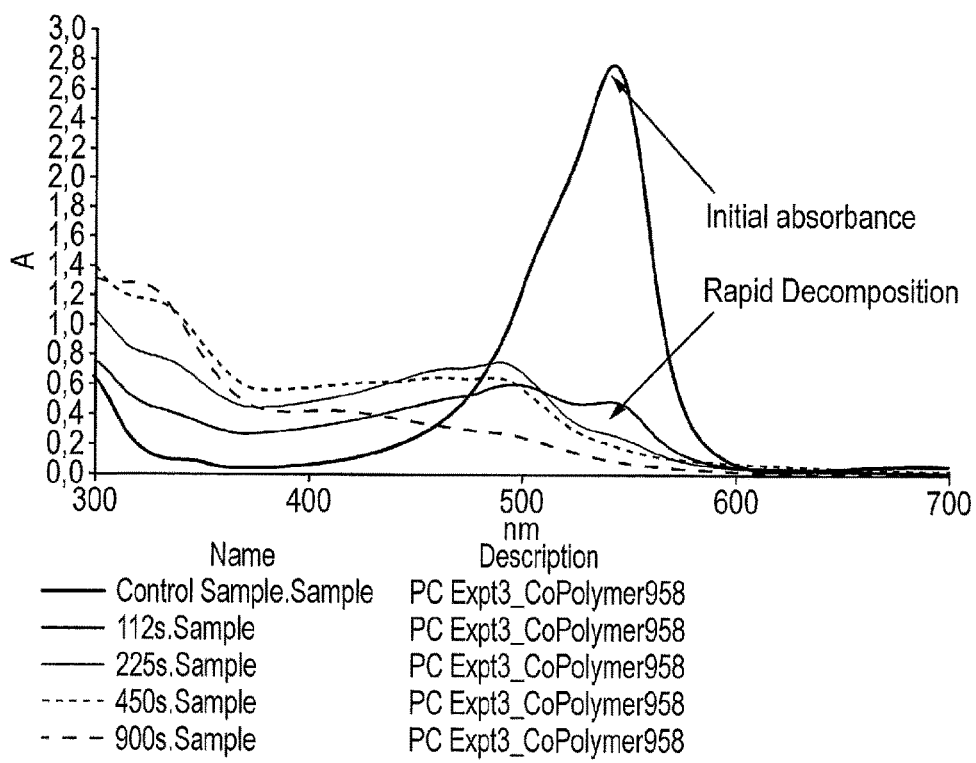
FIG. 21 schematically illustrates the UV/visible absorption spectrum of Basic Red 2 in the presence of Polymer 2248A.
Figure 22:
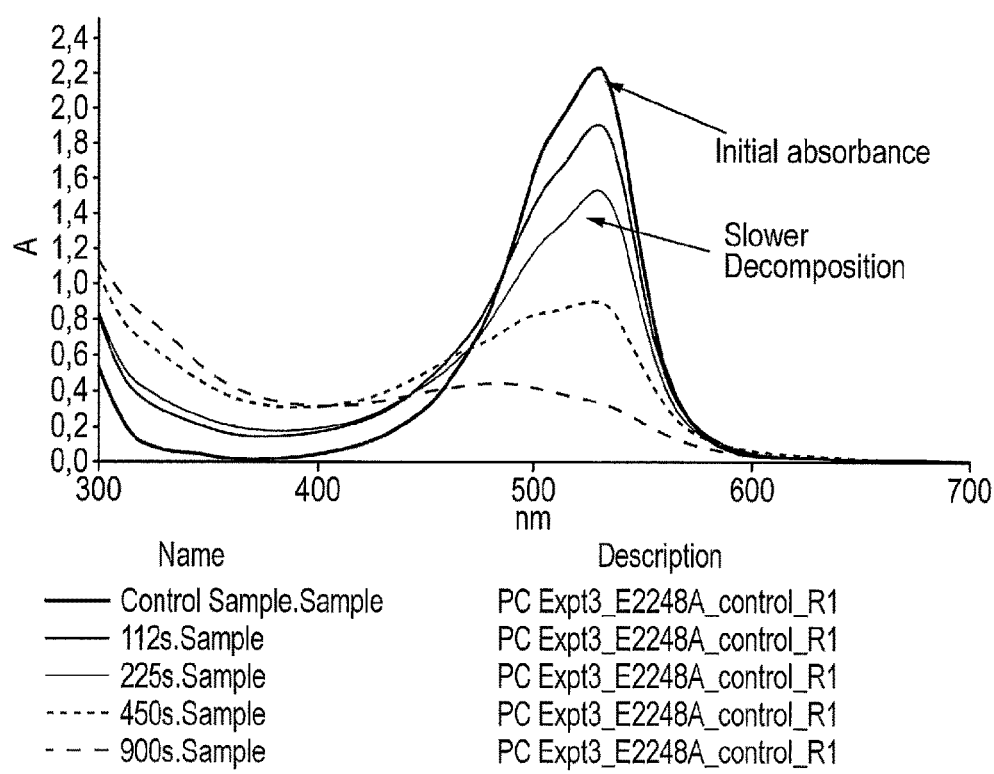
FIG. 22 schematically illustrates the UV/visible absorption spectrum of Basic Red 2 in the presence of Copolymer 958.

For the dye to efficiently participate in the photochemical reactions needed for photopolymerisation, the dye may be evenly distributed throughout the polymer and in close contact with the coinitiator. The spectra shown in FIGS. 21 and 22 show how dye decomposition can be controlled by the polymer support and by the amine coinitiator. The spectrum of the dye in the polymer support based on vinyl pyrrolidone copolymer has no evidence of aggregation and the dye is rapidly decomposed by irradiation.

Tests done involving the tertiary amine coinitiator show photobleaching of the dye at an intermediate rate, the addition of the tertiary amine however does not appear to influence dye aggregation and the dye gradually bleaches.

When the conductive liquid comprises nanoparticles (especially silver nanoparticles) and a visible light dye/coinitiator package, a vinyl lactam polymer may be used. The vinyl lactams lead to more effective curing because aggregation of the visible light absorbing dye is avoided and unwanted photophysical effects can be reduced.

All publications mentioned in the above specification are herein incorporated by reference. Various modifications and variations of the described methods and devices of the present technology will be apparent to those skilled in the art without departing from the scope and spirit of the present technology. Although the present technology has been described in connection with specific embodiments, it should be understood that the technology as claimed should not be unduly limited to such specific embodiments. Indeed, various modifications of the described modes for carrying out the technology which are obvious to those skilled in chemistry, physics and materials science or related fields are intended to be within the scope of the following claims.

The invention claimed is:

1. A method of manufacturing a device with a recessed electrode structure, the method comprising:
   providing a substrate with a microfluidic channel structure shaped to match the electrode structure;
   applying a primer layer to the microfluidic channel structure, thereby forming a primed microfluidic channel structure;
   spreading a conductive liquid to the primed microfluidic channel structure, the conductive liquid comprising a carrier medium, and the carrier medium comprising a solvent in which electrically conductive particles are dispersed;
   distributing the conductive liquid throughout the microfluidic channel structure by capillary action; and
   absorbing the solvent at least partially by the primer layer; and
   evaporating remaining solvent from the carrier medium to allow the electrically conductive particles to form the recessed electrode structure.

2. The method according to claim 1, further comprising after the evaporating:
   laminating the substrate with a cap layer to cover at least a part of the electrode structure.

3. The method according to claim 2, comprising after the laminating:
   applying radiation through the cap layer to cure a radiation curable monomer or prepolymer and thus harden the conductive liquid, wherein the carrier medium further comprises the radiation curable monomer or prepolymer.

4. The method according to claim 3, wherein the radiation curable monomer or prepolymer is curable with visible light.

5. The method according to claim 1, wherein the solvent is an organic solvent miscible with water.

6. The method according to claim 5, wherein the carrier medium further comprises water.

7. The method according to claim 5, wherein the organic solvent is an oxygenated solvent selected from the group consisting of an alcohol, a glycol ether, and a glycol ester.

8. The method according to claim 1, wherein the primer layer comprises:
   an organic polymer; and a porous particulate material, the porous particulate material being dispersed in the organic polymer.

9. The method according to claim 8, wherein the organic polymer in the primer layer is selected from the group consisting of:
   a polymer comprising a vinyl lactam repeating unit;
   a cellulose ether;
   a polyvinyl alcohol; and
   unmodified or modified gelatin.

10. The method according to claim 1, wherein during the providing, a pad is additionally formed on the substrate in fluid communicating with the microfluidic channel structure, and during the introducing, the conductive liquid is applied to the pad and distributed to the microfluidic channel structure by capillary action.

11. The method according to claim 1, wherein the substrate is an organic polymer.

12. The method according to claim 1, wherein the providing the substrate with the microfluidic channel structure is formed by injection moulding.

13. The method according to claim 1, wherein the applying the primer layer comprises:
   introducing a primer liquid to the microfluidic channel structure, the primer liquid comprising a primer carrier medium, and the primer carrier comprising a primer solvent; and
   waiting for the primer liquid to flow throughout the microfluidic channel structure by capillary action.

14. The method according to claim 1, wherein the primer layer comprises a porous particulate material and the primer layer does not include an organic polymer.

15. A device obtained by a method comprising the steps of:
   providing a substrate with a microfluidic channel structure shaped to match a recessed electrode structure;
   applying a primer layer to the microfluidic channel structure, thereby forming a primed microfluidic channel structure;
   spreading a conductive liquid to the primed microfluidic channel structure, the conductive liquid comprising a carrier medium, and the carrier medium comprising a solvent in which electrically conductive particles are dispersed;
   distributing the conductive liquid to flow throughout the microfluidic channel structure by capillary action; and
   absorbing the solvent at least partially by the primer layer; and
   evaporating remaining solvent from the carrier medium to allow the electrically conductive particles to form the recessed electrode structure.

* * * * *